United States Patent
Shin et al.

(10) Patent No.: US 10,428,386 B2
(45) Date of Patent: Oct. 1, 2019

(54) GENE FOR PREDICTING THE PROGNOSIS FOR EARLY-STAGE BREAST CANCER, AND A METHOD FOR PREDICTING THE PROGNOSIS FOR EARLY-STAGE BREAST CANCER BY USING THE SAME

(71) Applicant: Gencurix Inc., Seoul (KR)

(72) Inventors: Young Kee Shin, Seoul (KR); Young-Deug Kim, Incheon (KR); En Sel Oh, Seoul (KR); Si Eun Kim, Seoul (KR)

(73) Assignee: GENCURIX INC., Seoul (KR)

( * ) Notice: Subject to any disclaimer, the term of this patent is extended or adjusted under 35 U.S.C. 154(b) by 108 days.

(21) Appl. No.: 15/285,194

(22) Filed: Oct. 4, 2016

(65) Prior Publication Data

US 2017/0159126 A1 Jun. 8, 2017
US 2019/0017121 A9 Jan. 17, 2019

Related U.S. Application Data

(60) Division of application No. 13/935,502, filed on Jul. 4, 2013, now abandoned, which is a continuation of application No. PCT/KR2012/000021, filed on Jan. 2, 2012.

(30) Foreign Application Priority Data

Jan. 4, 2011 (KR) ........................ 10-2011-0000521

(51) Int. Cl.
*C12Q 1/68* (2018.01)
*C12Q 1/6886* (2018.01)
*G16B 25/00* (2019.01)
*G01N 33/574* (2006.01)

(52) U.S. Cl.
CPC ..... *C12Q 1/6886* (2013.01); *G01N 33/57415* (2013.01); *G01N 33/57484* (2013.01); *G16B 25/00* (2019.02); *C12Q 2600/118* (2013.01); *C12Q 2600/158* (2013.01); *G01N 2333/723* (2013.01)

(58) Field of Classification Search
None
See application file for complete search history.

(56) References Cited

PUBLICATIONS

Tabellini et al; Blood, vol. 108, abstract, Dec. 2006.*
Suzuki et al; Molecular Oncology, vol. 1, pp. 172-180; 2007.*

* cited by examiner

*Primary Examiner* — Jehanne S Sitton
(74) *Attorney, Agent, or Firm* — Cantor Colburn LLP

(57) ABSTRACT

The present invention relates to a method for selecting a gene intended to predict the prognosis for a cancer, to the selected gene for predicting the prognosis of cancer and to a kit for predicting and a method for predicting metastasis in breast-cancer patients by using the same. In the present invention, a straight forward method is used to achieve high-reliability prediction of the patient's prognosis by analyzing for the genetic characteristics of early stage breast cancer, and thus the present invention can be used to advantage in prognosis diagnosis which can reduce unnecessary anticancer therapy.

3 Claims, 24 Drawing Sheets

Specification includes a Sequence Listing.

FIG. 1

| Platform | GEO number | Year | Total | No. of LNN | No. of event | Survival type | Median f/u (yr) | Sample sources | Date of Dx | Treatment |
|---|---|---|---|---|---|---|---|---|---|---|
| Affymetrix U133A | GSE2034 | 2005 | 286 | 286 | 107 | DMFS | 7.17 | Erasmus Medical Center, The Netherlands | 1980–1995 | No systemic adjuvant therapy |
| | GSE6532 | 2006 | 284 | 179 | 65 | DMFS | 5.91 | John Radcliffe Hospital, UK; Guys Hospital, UK; Uppsala Univ. Hospital, Sweden | 1987–1989 | Tamoxifen only |
| | GSE7390 | 2006 | 198 | 198 | 62 | DMFS | 12.01 | Institut Gustave Roussy, France; Karolinska Institute, Sweden; Guys Hospital, UK; John Radcliffe Hospital, UK; Centre Rene Huguenin, France | 1980–1993 | No systemic adjuvant therapy |
| | GSE11121 | 2008 | 200 | 200 | 46 | DMFS | 7.54 | Johannes Guteberg Univ., Germany | 1988–1998 | No systemic adjuvant therapy |
| | GSE12093 | 2008 | 136 | 136 | 20 | DMFS | 7.06 | Ljubljana, Slovenia; National Cancer Institute, Italy; Technische Univ. Muenchen, Germany; Cleveland Clinic Foundation, US | 1981–2000 | Tamoxifen only |
| | GSE1456 | 2005 | 159 | Few | 40 | OS | 7.05 | Karolinska Hospital, Sweden | 1994–1996 | Tamoxifen + chemotherapy (104) |
| | GSE2494 | 2005 | 108 | 75 | 19 | OS | 10.17 | Uppsala Univ. Hospital, Sweden | 1987–1989 | For all node-positive patients, chemotherapy or tamoxifen |
| | GSE17705 | 2010 | 195 | 110 | 53 | DMFS | 9.41 | M.D. Anderson, USA; Institut Jules Bordet, Belgium | 1978–2002 | All tamoxifen only for 5 yrs |
| Agilent Hu25K | van de Vijver | 2002 | 295 | 151 | 101 | DMFS | 6.61 | Netherlands Cancer Institute, The Netherlands | 1984–1995 | For node-positive patients: -Chemotherapy only(90) -Tamoxifen only (30) -Both (20) |

Discovery data set: GSE2034, GSE6532, GSE7390, GSE11121, GSE12093
Validation data set 1: GSE1456
Validation data set 2: GSE2494
Validation data set 3: GSE17705, van de Vijver

FIG. 8

| model | df | Log-normal AIC | Log-logistic AIC | Weibull AIC |
|---|---|---|---|---|
| ① p.mean | 1 | 2450 | 2478 | 2506 |
| ② i.mean | 1 | 2518 | 2541 | 2553 |
| ③ p.mean + i.mean | 2 | 2433 | 2456 | 2487 |

SEQUENCE LISTING

<160> NUMBER OF SEQ ID NOS: 9

<210> SEQ ID NO 1
<211> LENGTH: 3128
<212> TYPE: DNA
<213> ORGANISM: Homo sapiens

<400> SEQUENCE: 1

| | | | | | |
|---|---|---|---|---|---|
| gcttcgcccc | gtggcgcggt | ttgaaatttt | gcggggctca | acggctcgcg gagcggctac | 60 |
| gcggagtgac | atcgccggtg | tttgcgggtg | gttgttgctc | tcggggccgt gtggagtagg | 120 |
| tctggacctg | gactcacggc | tgcttggagc | gtccgccatg | aggagaagtg aggtgctggc | 180 |
| ggaggagtcc | atagtatgtc | tgcagaaagc | cctaaatcac | cttcgggaaa tatgggagct | 240 |
| aattgggatt | ccagaggacc | agcggttaca | aagaactgag | gtggtaaaga agcatatcaa | 300 |
| ggaactcctg | gatatgatga | ttgctgaaga | ggaaagcctg | aaggaaagac tcatcaaaag | 360 |
| catatccgtc | tgtcagaaag | agctgaacac | tctgtgcagc | gagttacatg ttgagccatt | 420 |
| tcaggaagaa | ggagagacga | ccatcttgca | actagaaaaa | gatttgcgca cccaagtgga | 480 |
| attgatgcga | aaacagaaaa | aggagagaaa | acaggaactg | aagctacttc aagagcaaga | 540 |
| tcaagaactg | tgcgaaattc | tttgtatgcc | ccactatgat | attgacagtg cctcagtgcc | 600 |
| cagcttagaa | gagctgaacc | agttcaggca | acatgtgaca | actttgaggg aaacaaaggc | 660 |
| ttctaggcgt | gaggagtttg | tcagtataaa | gagacagatc | atactgtgta tggaagaatt | 720 |
| agaccacacc | ccagacacaa | gctttgaaag | agatgtggtg | tgtgaagacg aagatgcctt | 780 |
| ttgtttgtct | ttggagaata | ttgcaacact | acaaaagttg | ctacggcagc tggaaatgca | 840 |
| gaaatcacaa | aatgaagcag | tgtgtgaggg | gctgcgtact | caaatccgag agctctggga | 900 |
| caggttgcaa | atacctgaag | aagaaagaga | agctgtggcc | accattatgt ctgggtcaaa | 960 |
| ggccaaggtc | cggaaagcgc | tgcaattaga | agtggatcgg | ttggaagaac tgaaaatgca | 1020 |
| aaacatgaag | aaagtgattg | aggcaattcg | agtggagctg | gttcagtact gggaccagtg | 1080 |
| cttttatagc | caggagcaga | gacaagcttt | tgccccttc | tgtgctgagg actacacaga | 1140 |
| aagtctgctc | cagctccacg | atgctgagat | tgtgcggtta | aaaaactact atgaagttca | 1200 |
| caaggaactc | tttgaaggtg | tccagaagtg | ggaagaaacc | tggaggcttt tcttagagtt | 1260 |
| tgagagaaaa | gcttcagatc | caaatcgatt | tacaaaccga | ggaggaaatc ttctaaaaga | 1320 |
| agaaaaacaa | cgagccaagc | tccagaaaat | gctgcccaag | ctggaagaag agttgaaggc | 1380 |
| acgaattgaa | ttgtgggaac | aggaacattc | aaaggcattt | atggtgaatg ggcagaaatt | 1440 |
| catggagtat | gtggcagaac | aatgggagat | gcatcgattg | gagaaagaga gagccaagca | 1500 |
| ggaaagacaa | ctgaagaaca | aaaacagac | agagacagag | atgctgtatg gcagcgctcc | 1560 |
| tcgaacacct | agcaagcggc | gaggactggc | tcccaataca | ccgggcaaag cacgtaagct | 1620 |
| gaacactacc | accatgtcca | atgctacggc | caatagtagc | attcggccta tctttggagg | 1680 |
| gacagtctac | cactcccccg | tgtctcgact | tcctccttct | ggcagcaagc cagtcgctgc | 1740 |
| ttccacctgt | tcagggaaga | aaacaccccg | tactggcagg | catggagcca acaaggagaa | 1800 |
| cctggagctc | aacggcagca | tcctgagtgg | tgggtaccct | ggctcggccc ccctccagcg | 1860 |
| caacttcagc | attaattctg | ttgccagcac | ctattctgag | tttgcgaagg atccgtccct | 1920 |
| ctctgacagt | tccactgttg | ggcttcagcg | agaactttca | aaggcttcca atctgatgc | 1980 |
| tacttctgga | atcctcaatt | caaccaacat | ccagtcctga | gaagccctga tcagtcaacc | 2040 |
| agctgtggct | tcctgtgcct | agactggacc | taattatatg | ggggtgactt tagtttttct | 2100 |

```
tcagcttagg cgtgcttgaa accttggcca ggttccatga ccatgggcct aacttaaaga    2160
tgtgaatgag tgttacagtt gaaagcccat cataggttta gtggtcctag agacttggt    2220 tttgacttat atacatgaaa agtttatggc aagaagtgca aattttagca tatggggcct    2280
gacttctcta ccacataatt ctacttgctg aagcatgatc aaagcttgtt ttatttcacc    2340
actgtaggaa aatgattgac tatgcccatc cctgggggta attttggcat gtatacctgt    2400
aactagtaat taacatcttt tttgtttagg catgttcaat taatgctgta gctatcatag    2460
ctttgctctt acctgaagcc ttgtccccac cacacaggac agccttcctc ctgaagagaa    2520
tgtctttgtg tgtccgaagt tgagatggcc tgccctactg ccaaagaggt gacaggaagg    2580
ctgggagcag ctttgttaaa ttgtgttcag ttctgttaca cagtgcattg ccctttgttg    2640
ggggtatgca tgtatgaaca cacatgcttg tcggaacgct ttctcggcgt ttgtcccttg    2700
gctctcatct cccccattcc tgtgcctact ttgcctgagt tcttctaccc ccgcagttgc    2760
cagccacatt gggagtctgt ttgttccaat gggttgagct gtcttgtcg tggagatctg    2820 gaactttgca catgtcacta ctggggaggt gttcctgctc tagcttccac gatgaggcgc    2880
cctctttacc tatcctctca atcactactc ttcttgaagc actattattt attcttccgc    2940
tgtctgcctg cagcagtact actgtcaaca tagtgtaaat ggttctcaaa agcttaccag    3000
tgtggacttg gtgttagcca cgctgtttac tcatacagta cgtgtcctgt ttttaaaata    3060
tacaattatt cttaaaaata aattaaaatc tgtatactta catttcaaaa agaaaaaaaa    3120
aaaaaaaa                                                             3128

<210> SEQ ID NO 2
<211> LENGTH: 823
<212> TYPE: DNA
<213> ORGANISM: Homo sapiens

<400> SEQUENCE: 2
aaacgcgggc gggcgggccc gcagtcctgc agttgcagtc gtgttctccg agttcctgtc      60
tctctgccaa cgccgcccgg atggcttccc aaaaccgcga cccagccgcc actagcgtcg     120
ccgccgcccg taaaggagct gagccgagcg ggggcgccgc ccggggtccg gtgggcaaaa     180
ggctacagca ggagctgatg acccctcatga tgtctggcga taaagggatt tctgccttcc     240
ctgaatcaga caacctttc aaatgggtag ggaccatcca tggagcagct ggaacagtat     300
atgaagacct gaggtataag ctctcgctag agttccccag tggctaccct tacaatgcgc     360
ccacagtgaa gttcctcacg ccctgctatc accccaacgt ggacacccag ggtaacatat     420
gcctggacat cctgaaggaa aagtggtctg ccctgtatga tgtcaggacc attctgctct     480
ccatccagag ccttctagga gaacccaaca ttgatagtcc cttgaacaca catgctgccg     540
agctctggaa aaaccccaca gcttttaaga agtacctgca agaaacctac tcaaagcagg     600
tcaccagcca ggagccctga cccaggctgc ccagcctgtc cttgtgtcgt cttttttaatt     660 tttccttaga tggtctgtcc ttttttgtgat ttctgtatag gactctttat cttgagctgt     720 ggtattttg ttttgttttt gtcttttaaa ttaagcctcg gttgagccct tgtatattaa     780
ataaatgcat ttttgtcctt ttttagacaa aaaaaaaaa aaa                        823

<210> SEQ ID NO 3
<211> LENGTH: 1530
<212> TYPE: DNA
<213> ORGANISM: Homo sapiens
```

<400> SEQUENCE: 3

```
aatcctggaa caaggctaca gcgtcgaaga tccccagcgc tgcgggctcg gagagcagtc      60
ctaacggcgc ctcgtacgct agtgtcctcc cttttcagtc cgcgtccctc cctgggccgg     120
gctggcactc ttgccttccc cgtccctcat ggcgctgctc cgacgcccga cggtgtccag     180
tgatttggag aatattgaca caggagttaa ttctaaagtt aagagtcatg tgactattag     240
gcgaactgtt ttagaagaaa ttggaaatag agttacaacc agagcagcac aagtagctaa     300
gaaagctcag aacaccaaag ttccagttca acccaccaaa acaacaaatg tcaacaaaca     360
actgaaacct actgcttctg tcaaaccagt acagatggaa aagttggctc aaagggtcc      420
ttctcccaca cctgaggatg tctccatgaa ggaagagaat ctctgccaag cttttttctga    480
tgccttgctc tgcaaaatcg aggacattga taacgaagat tgggagaacc ctcagctctg     540
cagtgactac gttaaggata tctatcagta tctcaggcag ctggaggttt tgcagtccat     600
aaacccacat tcttagatg aagagatat aaatggacgc atgcgtgcca tcctagtgga      660
ttggctggta caagtccact ccaagtttag gcttctgcag gagactctgt acatgtgcgt     720
tggcattatg gatcgatttt tacaggttca gccagttcc ggaagaagc ttcaattagt      780
tgggattact gctctgctct tggcttccaa gtatgaggag atgttttctc caaatattga     840
agactttgtt tacatcacag acaatgctta taccagttcc caaatccgag aaatggaaac     900
tctaattttg aaagaattga aatttgagtt gggtcgaccc ttgccactac acttcttaag     960
gcgagcatca aaagccgggg aggttgatgt tgaacagcac actttagcca agtattgat   1020
gagctgact ctcatcgact atgatatggt gcattatcat ccttctaagg tagcagcagc    1080
tgcttcctgc ttgtctcaga aggttctagg acaaggaaaa tggaacttaa agcagcagta    1140
ttacacagga tacacagaga atgaagtatt ggaagtcatg cagcacatgg ccaagaatgt    1200
ggtgaaagta aatgaaaact taactaaatt catcgccatc aagaataagt atgcaagcag    1260
caaactcctg aagatcagca tgatccctca gctgaactca aaagccgtca agaccttgc    1320
ctcccactg ataggaaggt cctaggctgc cgtgggccct ggggatgtgt gcttcattgt     1380
gccctttttc ttattggttt agaactcttg attttgtaca tagtcctctg gtctatctca    1440
tgaaacctct tctcagacca gttttctaaa catatattga ggaaaaataa agcgattggt    1500
ttttcttaag gtaaaaaaaa aaaaaaaaaa                                     1530
```

<210> SEQ ID NO 4
<211> LENGTH: 1697
<212> TYPE: DNA
<213> ORGANISM: Homo sapiens

<400> SEQUENCE: 4

```
gaggcgtaag ccaggcgtgt taaagccggt cggaactgct ccggagggca cgggctccgt      60
aggcaccaac tgcaaggacc cctcccctg cgggcgctcc catggcacag ttcgcgttcg     120
agagtgacct gcactcgctg cttcagctgg atgcacccat ccccaatgca ccccctgcgc     180
gctggcagcg caaagccaag gaagccgcag gcccggcccc ctcacccatg cgggccgcca     240
accgatccca cagcgccggc aggactccgg gccgaactcc tggcaaatcc agttccaagg     300
ttcagaccac tcctagcaaa cctggcggtg accgctatat ccccatcgc agtgctgccc     360
agatggaggt ggccagcttc ctcctgagca aggagaacca gcctgaaaac agccagacgc     420
ccaccaagaa ggaacatcag aaagcctggg cttttgaacct gaacggtttt gatgtagagg     480
aagccaagat ccttcggctc agtggaaaac cacaaaatgc gccagagggt tatcagaaca    540
```

```
gactgaaagt actctacagc caaaaggcca ctcctggctc cagccggaag acctgccgtt    600
acattccttc cctgccagac cgtatcctgg atgcgcctga atccgaaat gactattacc    660 tgaaccttgt ggattggagt tctgggaatg tactggccgt ggcactggac aacagtgtgt    720
acctgtggag tgcaagctct ggtgacatcc tgcagctttt gcaaatggag cagcctgggg    780
aatatatatc ctctgtggcc tggatcaaag agggcaacta cttggctgtg gcaccagca    840 gtgctgaggt gcagctatgg gatgtgcagc agcagaaacg gcttcgaaat atgaccagtc    900
actctgcccg agtgggctcc ctaagctgga acagctatat cctgtccagt ggttcacgtt    960
ctggccacat ccaccaccat gatgttcggg tagcagaaca ccatgtggcc acactgagtg   1020
gccacagcca ggaagtgtgt gggctgcgct gggccccaga tggacgacat ttggccagtg   1080
gtggtaatga taacttggtc aatgtgtggc ctagtgctcc tggagagggt ggctgggttc   1140
ctctgcagac attcacccag catcaagggg ctgtcaaggc cgtagcatgg tgtccctggc   1200
agtccaatgt cctggcaaca ggaggggggca ccagtgatcg acacattcgc atctggaatg   1260
tgtgctctgg ggcctgtctg agtgccgtgg atgcccattc ccaggtgtgc tccatcctct   1320
ggtctcccca ttacaaggag ctcatctcag gccatggctt tgcacagaac cagctagtta   1380 tttgaagta cccaaccatg gccaaggtgg ctgaactcaa aggtcacaca tcccgggtcc   1440
tgagtctgac catgagccca gatggggcca cagtggcatc cgcagcagca gatgagaccc   1500
tgaggctatg cgctgttttt gagttggacc ctgcgcggcg gcgggagcgg gagaaggcca   1560
gtgcagccaa aagcagcctc atccaccaag gcatccgctg aagaccaacc catcacctca   1620
gttgtttttt attttctaa taaagtcatg tctcccttca tgtttttttt ttaaaaaaa    1680 aaaaaaaaaa aaaaaaa                                                  1697

<210> SEQ ID NO 5
<211> LENGTH: 771
<212> TYPE: DNA
<213> ORGANISM: Homo sapiens

<400> SEQUENCE: 5
agagaagcag acatcttcta gttcctcccc cactctcctc tttccggtac ctgtgagtca     60
gctaggggag ggcagctctc acccaggctg atagttcggt gacctggctt tatctactgg    120
atgagttccg ctgggagatg gaacatagca cgtttctctc tggcctggta ctggctaccc    180
ttctctcgca agtgagcccc ttcaagatac ctatagagga acttgaggac agagtgtttg    240
tgaattgcaa taccagcatc acatgggtag agggaacggt gggaacactg ctctcagaca    300
ttacaagact ggacctggga aaacgcatcc tggacccacg aggaatatat aggtgtaatg    360
ggacagatat atacaaggac aaagaatcta ccgtgcaagt tcattatcga atgtgccaga    420
gctgtgtgga gctggatcca gccaccgtgg ctggcatcat tgtcactgat gtcattgcca    480
ctctgctcct tgctttggga gtcttctgct ttgctggaca tgagactgga aggctgtctg    540
gggctgccga cacacaagct ctgttgagga atgaccaggt ctatcagccc ctccgagatc    600
gagatgatgc tcagtacagc caccttggag gaaactgggc tcggaacaag tgaacctgag    660
actggtggct tctagaagca gccattacca actgtacctt cccttcttgc tcagccaata    720
aatatatcct ctttcactca gaaaaaaaa aaaaaaaaa aaaaaaaaa a                 771

<210> SEQ ID NO 6
<211> LENGTH: 1270
<212> TYPE: DNA
```

<213> ORGANISM: Homo sapiens

<400> SEQUENCE: 6

```
attttctaaa agggacagag agcaccctgc tacatttcct aatcaagaag ttggcgtgca      60
gctgggagag ctagactaag ttggtcatga tgcagaagct actcaaatgc agtcggcttg     120
tcctggctct tgccctcatc ctggttctgg aatcctcagt tcaaggttat cctacgcgga     180
gagccaggta ccaatgggtg cgctgcaatc cagacagtaa ttctgcaaac tgccttgaag     240
aaaaaggacc aatgttcgaa ctacttccag gtgaatccaa caagatcccc cgtctgagga     300
ctgaccttTT tccaaagacg agaatccagg acttgaatcg tatcttccca ctttctgagg     360
actactctgg atcaggcttc ggctccggct ccggctctgg atcaggatct gggagtggct     420
tcctaacgga aatggaacag gattaccaac tagtagacga aagtgatgct ttccatgaca     480
accttaggtc tcttgacagg aatctgccct cagacagcca ggacttgggt caacatggat     540
tagaagagga ttttatgtta taaagagga ttttcccacc ttgacaccag caatgtagt       600
tagcatattt tatgtaccat ggttatatga ttaatcttgg acaaagaat tttatagaaa       660
tttttaaaca tctgaaaaag aagcttaagt tttatcatcc ttttttttct catgaattct      720
taaaggatta tgctttaatg ctgttatcta ttttattgtt cttgaaaata cctgcatttt     780
ttggtatcat gttcaaccaa catcattatg aaattaatta gattcccatg gccataaaat     840
ggctttaaag aatatatata tatttttaaa gtagcttgag aagcaaattg gcaggtaata     900
tttcatacct aaattaagac tctgacttgg attgtgaatt ataatgatat gccccttttc     960
ttataaaaac aaaaaaaaaa ataatgaaac acagtgaatt tgtagagtgg gggtatttga    1020
catattttac agggtggagt gtactatata ctattacctt tgaatgtgtt tgcagagcta    1080
gtggatgtgt ttgtctacaa gatgattgc tgttacataa cacccccaaat taactcccaa    1140
attaaaacac agttgtgctg tcaatacctc atactgcttt accttttttt cctggatatc    1200
tgtgtatttt caaatgttac tatatattaa agcagaaata taaccaaagg ttaaaaaaaa    1260
aaaaaaaaa                                                            1270
```

<210> SEQ ID NO 7
<211> LENGTH: 523
<212> TYPE: DNA
<213> ORGANISM: Homo sapiens

<400> SEQUENCE: 7

```
ctcctggttc aaaagcagct aaaccaaaag aagcctccag acagccctga gatcacctaa      60
aaagctgcta ccaagacagc cacgaagatc ctaccaaaat gaagcgcttc ctcttcctcc     120
tactcaccat cagcctcctg gttatggtac agatacaaac tggactctca ggacaaaacg     180
acaccagcca aaccagcagc ccctcagcat ccagcaacat aagcggaggc attttccttt     240
tcttcgtggc caatgccata atccacctct tctgcttcag ttgaggtgac acgtctcagc     300
cttagccctg tgccccctga aacagctgcc accatcactc gcaagagaat cccctccatc     360
tttgggaggg gttgatgcca gacatcacca ggttgtagaa gttgacaggc agtgccatgg     420
ggcaacagc caaataggg gggtaatgat gtagggccca agcagtgccc agctgggggt      480
caataaagtt acccttgtac ttgcaaaaaa aaaaaaaaaa aaa                       523
```

<210> SEQ ID NO 8
<211> LENGTH: 684
<212> TYPE: DNA
<213> ORGANISM: Homo sapiens

```
<400> SEQUENCE: 8
cattcccagc ctcacatcac tcacaccttg catttcaccc ctgcatccca gtcgccctgc      60
agcctcacac agatcctgca cacacccaga cagctggcgc tcacacattc accgttggcc     120
tgcctctgtt caccctccat ggccctgcta ctggccctca gctgctggt tctctggact     180
tccccagccc caactctgag tggcaccaat gatgctgaag actgctgcct gtctgtgacc     240
cagaaaccca tccctgggta catcgtgagg aacttccact accttctcat caaggatggc     300
tgcagggtgc ctgctgtagt gttcaccaca ctgagggggcc gccagctctg tgcaccccca     360
gaccagccct gggtagaacg catcatccag agactgcaga ggacctcagc caagatgaag     420
cgccgcagca gttaacctat gaccgtgcag agggagcccg gagtccgagt caagcattgt     480
gaattattac ctaacctggg gaaccgagga ccagaaggaa ggaccaggct tccagctcct     540
ctgcaccaga cctgaccagc caggacaggg cctggggtgt gtgtgagtgt gagtgtgagc     600
gagagggtga gtgtggtcag agtaaagctg ctccacccccc agattgcaat gctaccaata     660
aagccgcctg gtgtttacaa ctaa                                            684

<210> SEQ ID NO 9
<211> LENGTH: 293
<212> TYPE: DNA
<213> ORGANISM: Homo sapiens

<400> SEQUENCE: 9
ggtgctgtcg tctctcaaca tccgagctgg gttatctgta agagtggaac ctctgtgaag      60
atcgagtgcc gttccctgga ctttcaggcc acaactatgt tttggtatcg tcagttcccg     120
aaacagagtc tcatgctgat ggcaacttcc aatgagggct ccaaggccac atacgagcaa     180
ggcgtcgaga aggacaagtt tctcatcaac catgcaagcc tgaccttgtc cactctgaca     240
gtgaccagtg cccatcctga agacagcagc ttctacatct gcagtgctag aga             293
```

GENE FOR PREDICTING THE PROGNOSIS FOR EARLY-STAGE BREAST CANCER, AND A METHOD FOR PREDICTING THE PROGNOSIS FOR EARLY-STAGE BREAST CANCER BY USING THE SAME

CROSS-REFERENCE TO RELATED APPLICATIONS

This application is a divisional application of U.S. application Ser. No. 13/935,502 filed on Jul. 4, 2013, which is a continuation of International Application No. PCT/KR2012/000021 filed on Jan. 2, 2012, which claims priority to Korean Application No. 10-2011-0000521 filed on Jan. 4, 2011. The entire contents of the aforementioned patent applications are incorporated herein by reference.

SEQUENCE LISTING

The instant application contains a Sequence Listing which has been submitted in ASCII format via EFS-Web with regard to U.S. application Ser. No. 13/935,502 and is hereby incorporated by reference in its entirety. Said ASCII copy, created on Nov. 23, 2016, is named 48116-540D01US_ST25.txt and is 15,305 bytes in size.

FIELD OF THE INVENTION

The present invention relates to a development of a prognostic gene and a method for predicting prognosis of the early stage breast cancer.

DESCRIPTION OF THE RELATED ART

As human genome information has been utilizing actively, cancer researches tens to identify mechanism at genome level. In particular, microarray is able to identify cancer cell properties in a macroscopic view, on the basis of information for tens of thousands of microarray gene expression patterns or increase or decrease of the number of genes. Analyzing this genome level information is a very innovative way to understand intimately complicated life phenomena and it will be more activated. Particularly, in the case of complex diseases such as cancer, analysis for a small number of specific genes is likely to obtain a blinkered result. In addition, since capturing whole behavior patterns for oncogenesis and development of cancer is important, genome information analysis is necessary. Like this, most of genome information which is a basis for cancer research is produced using genome chip such as microarray. Technologies able to get information for tens of thousands of genes are evolving day by day. In spite of the disadvantages of high cost, researches using microarray are actively developed such that amounts of related information are explosively increasing. From the middle of in the year 2000, this genome information began to be collected into a database, whereby secondary and tertiary analysis using the information are becoming a focal point for researches of phenomenon of life.

In general expression gene chip, tens of thousands of probes representing approximately 20,000 to 30,000 genes are immobilized. In microarray measuring precisional information such as SNP, more than one million of probes are immobilized. Method of microarray is very efficient since it is relatively simple, standardized and a large amount of information may be obtained in a short time at once. However, analyzing results are key point as well as drawback. Comprehensive analysis for tens of thousands of genes incomparable to existing analysis for a small number of genes must be supported by wide knowledge and statistical analysis techniques for genome, whereby information eventually becomes useful. Besides, high-performance computing equipment is required to store and analyze large amounts of information, and the related computational techniques are also required. However, since it is difficult to perform to the researchers who familiar with traditional biological research range and experimental methods, it is not utilized usefully. Therefore, utilizing the released genome information serves a very valuable purpose. Particularly, researches for cancer have been actively introduced, whereby a considerable amount of related-information has been accumulated.

Breast cancer is possible for self-diagnosis and the importance of self-diagnosis is promoted such that breast cancer may be found in the early-stage. It is difficult to decide whether this early-stage breast cancer patients after surgery receive treatments for anticancer. Although it is possible to predict for an approximate prognosis by pathological observation, the observation result is difficult to standardize and quantify, and its reliability is low. For these reasons, it is recommended that most of patients with the early-stage breast cancer should have clinical anticancer treatments. Due to the nature of anticancer treatments, patients suffer from a huge pain and financial expenditure. It is supposed that the patients not required anticancer treatments are to be more than half of the early-stage breast cancer patients. Therefore, if unnecessary anticancer treatments are reduced by predicting prognosis of patient with analysis to the characteristics of the early-stage breast cancer, it may be a great help to life quality of patients.

As the information about tens of thousands of breast cancer gene expression patterns may be obtained using microarray at once, researches for classifying breast cancer at molecular level and revealing mechanism to cancer occurrence and development are actively carried out. It is important to predict prognosis of the early stage breast cancer patient in clinic. To develop gene for predicting prognosis using microarrays has been began already in the early 2000s.

Although researches using microarray are required high-costs, a significant number of breast cancer tissue expression profiles have been produced and opened to researchers. Starting from the development of 70 genes for predicting prognosis by analyzing the early stage breast cancer tissues and survival data followed for 10 years of 78 people in 2002, a dozen genes for predicting prognosis were published. Among them, several genes have already commercialized and used in clinic (1-13). As representatives of those, MammaPrint® (Agendia) and Oncotype DX® (Genomic Health) have been currently used in clinic. However, they have been still used as one of references to prognosis (2, 7).

Throughout this application, various patents and publications are referenced and citations are provided in parentheses. The disclosure of these patents and publications in their entities are hereby incorporated by references into this application in order to more fully describe this invention and the state of the art to which this invention pertains.

DETAILED DESCRIPTION OF THIS INVENTION

Technical Purposes of this Invention

The present inventors have made intensive researches to develop gene diagnostic systems for predicting breast cancer prognosis with reliability in order to decide anticancer treatment for patients with the early-stage breast cancer. As a result, microarray data and clinical information obtained from the early-stage breast cancer tissue were collected and analyzed to develop genes related prognosis, whereby they have developed a prognostic model.

Accordingly, it is an object of this invention to provide a gene selection method for predicting cancer prognosis.

It is another object of this invention to provide a gene for predicting cancer prognosis.

It is still another object of this invention to provide a method for predicting cancer prognosis.

Other objects and advantages of the present invention will become apparent from the detailed description to follow taken in conjugation with the appended claims and drawings.

Technical Solutions of this Invention

In one aspect of the present invention, there is provided a method for selecting a gene for predicting the prognosis of a cancer, comprising:

(a) collecting cancer tissues from a patient group of which clinical information has been known;

(b) classifying the patient group into a poor prognosis group and a good prognosis group; wherein the poor prognosis group comprises patients in which metastasis occurs before a reference time point, and the good prognosis group comprises patients in which metastasis does not occur after the reference time point;

(c) obtaining expression profiles of genes from the collected cancer tissues;

(d) selecting genes showing difference in expression levels between the poor prognosis group and the good prognosis group;

(e) classifying the selected genes by expression patterns into gene clusters by use of a clustering analysis for expression patterns;

(f) selecting an expression pattern having significant correlation with certain function by performing a function analysis to the gene clusters classified by expression patterns; and (g) selecting a gene in genes belonging to the selected expression pattern; wherein the selected gene shows not only high expression level but also large difference in expression levels between the poor prognosis group and the good prognosis group.

The present inventors have made intensive researches to develop gene diagnostic systems for predicting breast cancer prognosis with reliability in order to decide anticancer treatment for patients with the early-stage breast cancer. As a result, microarray data and clinical information obtained from the early-stage breast cancer tissue were collected and analyzed to develop genes related prognosis, whereby they have developed a prognostic model.

The term "prognosis" as used herein refers symptoms in the future or prospects of progress determined by diagnosing a disease. Prognosis in patients with cancer means occurrence of metastasis or survival period after surgical procedures within certain period. Since prediction of prognosis in patients with the early-stage breast cancer, especially chemotherapy as well as the future direction of the clues for breast cancer treatment, it is a very important clinical challenge.

According to a preferred embodiment, the clinical information in the present step (a) comprises information for cancer metastasis state.

The term "metastasis" as used herein refers to a proliferating state that the primary cancer is transplanted to other parts of body by various routes to set and grow. Since occurrence of metastasis is determined by specific characteristics of the cancer, and it is an important clue in determining the prognosis of cancer, it is considered as the most important clinical information associated with the survival of cancer patients. According to the present invention, the cancer tissues are collected to obtain information about the patient's metastasis and differences of gene expression profiles between different groups in metastasis occurrence are analyzed such that prognostic marker genes may be selected.

In the present step (b), the reference time point is a period for determining the prognosis to cancer patients, it refers to a period to generation of cancer before the onset of metastasis. The reference time point is preferably 3 to 12 years after onset, and more preferably 5 to 10 years. In addition, it may be same or different period to classify a group as poor prognosis and good prognosis. Most preferably, the patients in metastasis occurred within 5 years after the onset in the patient population is classified as poor prognosis group, and the patients in metastasis no- occurred more than 10 years after the onset is classified as a good prognosis group.

In the present step (c), the term "expression profile" refers that activities of a lot of genes are simultaneously measured to obtain information about cell, tissue or organ function. Activity of gene includes transcription activity, translation activity, expression level of a protein produced and, and its activity in vivo.

Steps to collect the gene expression profiles may be carried out using, for example, microarray analysis, multiplex PCR (polymerase chain reaction), quantitative RT-PCR (reverse transcription polymerase chain reaction), transcriptome analysis using tiling array and short read sequencing, but not limited thereto, in various ways known in the art. Preferably it may be carried out by microarray analysis. To statistical analysis of the collected microarray expression profiles, various normalization methods conventionally used in the art may be used, and preferably RMA (Robust Multi-array Average) normalization method.

In the present step (d), the term "a difference in the expression level" means that specific gene expression level between the prognostic groups is significantly different when specific gene expression level between the prognostic groups are compared using microarray expression profile analysis (FDR<0.01).

The analysis of differences in expression levels may use a variety of methods commonly used in the art, preferably SAM (Significant Analysis of Microarray) analysis.

SAM analysis is an analysis using the microarray analysis algorithm SAM. The difference in expression levels between groups is calculated in the similar manner with T-test, and the significance of the difference in expression level is represented by FDR (false discovery rate, q-value). The smaller q-values, it is more significant in the difference of gene expression.

According to a preferred embodiment, the cancer is breast cancer, and more preferably the early-stage breast cancer.

According to a preferred embodiment, the method further includes, between the steps (a) and (b), the step of classifying the patient group into a patient group showing less than a reference expression level of estrogen receptor (ER) and a patient group showing more than a reference expression level of estrogen receptor (ER).

Expression occurrence of estrogen receptor is the most commonly used standard for classifying subtypes of breast cancer patients. It has been known that the lower expression level of estrogen receptors in breast cancer leads to be higher risk of metastasis of breast cancer. In clinic, pathologist divides into ER+ or ER− by reading the results of ER IHC (immuno-histochemistry). According to the present invention, the subject patient groups are classified according to the expression levels of the estrogen receptor, and classified as the ER positive group and the ER negative group to the good prognosis group and the poor prognosis group, respectively to analyze, whereby the genes showing significantly differential expression between the prognostic groups may be selected with more reliability.

The most preferably, the reference expression level to classify subtype (ER+ or ER−) for estrogen receptor (ER) is determined ROC (receiver-operating characteristics) analysis using ER IHC (estrogen receptor immuno-histochemistry) results or mRNA expression level of ESR 1 (estrogen receptor 1).

The term "clustering analysis" as used herein refers to a multivariate analysis method classifying subjects of analysis to cluster to verify the structural relationship between them.

In the present step (e), the clustering analysis may be carried out using various methods commonly used in the art, and preferably PCA (Principal Component Analysis). PCA analysis generates a small number of novel super-genes recombinated by linear combination with information of various gene variables. In other words, it is a method reducing dimensions by reducing the number of variables while loss of the original data is minimized.

The term "function analysis" as used herein refers verifying biological functions for the genes highly associated with the principal component selected in the step (e).

In the present step (f), the function analysis may be carried out using various method commonly used in the art, and preferably a GO (Gene Ontology) analysis.

In the present step (g), a prognostic gene selection may be selected according to the statistical significance, and preferably, it was selected by additionally considering the correlation with the selected principal component, the average expression level and the range of quartile besides the difference of the average expression level between prognostic groups. The term "higher expression levels" as used herein refers to a case that the average expression levels in gene groups belonging to the selected expression pattern is sufficiently high to allow statistical analysis, and preferably, it is selected in the order of the top-ranked gene in the expression level among the selected gene group. The term "large differences in expression levels" as used herein refers to a case that the differences of the average expression levels in gene groups belonging to the selected expression pattern is sufficiently distinct to allow experimental analysis, preferably, it is selected in the order of the top-ranked gene in the differences of the expression level between the prognostic groups among the selected gene group, and most preferably, it is selected in the order of the top-ranked gene in the expression level among the selected gene group and the top-ranked gene in the differences of the expression level between the prognostic groups among the selected gene group.

Preferably, the present invention may further include a step developing mathematical model for survival probability using the selected prognostic gene after the present step (g). This model development may be performed by mathematizing the relationship between times as long metastasis to occur and prognostic genes through survival regression analysis in which the selected prognostic gene is covariates. The relationship between times as long metastasis to occur and prognostic genes may be verified using a variety of survival models, and preferably parametric survival analysis AFT model. Preferably, the survival model developed using the selected prognostic genes may be verified in independent dataset. The validation method may compare to the survival probability and the actual observed survival probability. Moreover, where the prognostic groups are classified using the survival model, an accuracy of the validation method may be evaluated by comparing with the actual observed prognostic group.

In another aspect of the present invention, there is provided a kit for predicting metastasis risk of a breast cancer patient comprising a primer or a probe which is specifically hybridized with a nucleotide sequence selected from a group consisting of nucleotide sequences as set forth in SEQ ID NOs:1-9.

The term "nucleotide" as used herein refers to as deoxyribonucleotide or ribonucleotide that is present in a single-strand or double-strand form, and includes natural nucleotide analogues, unless stated otherwise (Scheit, Nucleotide Analogs, John Wiley, New York (1980); Uhlman and Peyman, Chemical Reviews, 90:543-584 (1990)).

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH. Preferably, the primer is deoxyribonucleotide and single stranded. The primer of this invention may be comprised of naturally occurring dNMP (i.e., dAMP, dGM, dCMP and dTMP), modified nucleotide, or non-natural nucleotide. The primer may also include ribonucleotides.

The present primer may be an extension primer forming a complementary sequence to a target nucleic acid by annealing to a target nucleic acid by template-dependent nucleic acid polymerase. The immobilized probe is extended to a site annealed probe to occupy.

The extension primer used in the present invention includes a hybridizing nucleotide sequence complementary to first site of a target nucleic acid sequence. The term "complementary" is used herein to mean that primers or probes are sufficiently complementary to hybridize selectively to a target nucleic acid sequence under the designated annealing conditions or hybridization conditions, encompassing the terms "substantially complementary" and "perfectly complementary", preferably perfectly complementary.

The term "substantially complementary" in conjunction with the primer sequence, the sequences of primers are not required to have perfectly complementary sequence to templates. The sequences of primers may comprise some mismatches, so long as they can be hybridized with templates and serve as primers.

The primer must be sufficiently long to prime the synthesis of extension products in the presence of the agent for polymerization. The suitable length of primers will depend on many factors, including temperature, application and source of primer, generally, 15-30 nucleotides in length. In general, shorter primers need lower temperature to form stable hybridization duplexes to templates. The term "annealing" or "priming" as used herein refers to the apposition of an oligodeoxynucleotide or nucleic acid to a template nucleic acid, whereby the apposition enables the polymerase to polymerize nucleotides into a nucleic acid molecule which is complementary to the template nucleic acid or a portion thereof.

The sequences of primers are not required to have perfectly complementary sequence to templates. The sequences of primers may comprise some mismatches, so long as they can be hybridized with templates and serve as primers. Therefore, the primers of this invention are not required to have perfectly complementary sequence to the nucleotide sequence as described above; it is sufficient that they have complementarity to the extent that they anneals specifically to the nucleotide sequence of the gene for acting as a point of initiation of synthesis. The primer design may be conveniently performed with referring to the above-described nucleotide sequences. For instance, the primer design may be carried out using computer programs for primer design (e.g., PRIMER3 program).

The term "nucleic acid molecule" as used herein refers to a comprehensive DNA (gDNA and cDNA) and RNA molecule, and a nucleotide as a basic unit in the nucleic acid includes not only natural nucleotides but also analogues which a sugar or base are modified (Scheit, Nucleotide Analogs, John Wiley, New York (1980); Uhlman and Peyman, Chemical Reviews, 90:543-584 (1990)).

Where a gRNA is employed as starting material in the present kit, an isolation of gDNA may be carried out according to conventional methods known in the art (see: Rogers & Bendich (1994)).

Where a mRNA is employed as starting material in the present kit, an isolation of total RNA may be carried out according to conventional methods known in the art (see: Sambrook, J. et al., Molecular Cloning. A Laboratory Manual, 3rd ed. Cold Spring Harbor Press (2001); Tesniere, C. et al., Plant Mol. Biol. Rep., 9:242 (1991); Ausubel, F. M. et al., Current Protocols in Molecular Biology, John Willey & Sons (1987); and Chomczynski, P. et al., Anal. Biochem. 162:156 (1987)). The isolated total RNA is synthesized to cDNA using reverse transcriptase. Since total RNA molecules used in the present invention are isolated from human samples, mRNA molecules have poly-A tails and converted to cDNA by use of dT primer and reverse transcriptase (see: PNAS USA, 85: 8998 (1988); Libert F, et al., Science, 244: 569 (1989); and Sambrook, J. et al., Molecular Cloning. A Laboratory Manual, 3rd ed. Cold Spring Harbor Press (2001)).

The investigation of the certain sequence in the present kit may be carried out according to the various methods known in the art. For example, techniques that may be used in the present invention includes, but is not particularly limited to, fluorescence in situ hybridization (FISH), direct DNA sequencing, PFGE analysis, Southern blotting analysis, single-strand conformation analysis (SSCA, Orita et al., PNAS, USA 86:2776 (1989)), RNase protection assay (Finkelstein et al., Genomics, 7:167 (1990)), dot-blot assay, denaturing gradient gel electrophoresis (DGGE, Wartell et al., Nucl. Acids Res., 18:2699 (1990)), a method using proteins (e.g, mutS protein from *E. coli*) which recognize nucleotide mismatches (Modrich, Ann. Rev. Genet., 25:229-253 (1991)), and allele-specific PCR.

The changes in sequences lead to the difference in the binding of single-stranded intracellular bases, resulting in appearance of bands with different mobility. At this time, the bands are detected using the SSCA. The sequences having mobility different from that of a wild-type sequence are also detected using the DGGE analysis or TDGS (Two-Dimensional Gene Scanning) analysis.

Other techniques are generally carried out using probes or primers which are complementary to the sequence including the nucleotides of the present invention.

For example, a riboprobe that is complementary to the sequence including the nucleotide of the present invention is used in the case of the RNase protection assay. The isolated DNA or mRNA is hybridized with the riboprobe, and then digested with an RNase A enzyme that can detect nucleotide mismatches. Smaller bands are observed if the nucleotide mismatches are recognized by the RNase A.

A probe complementary to the nucleotide of the present invention is used in the case of the analysis using a hybridization signal. Hybridization signals of the probe and a target sequence are detected to directly determine DM or MS in this technique.

As used herein, the term "probe" means a natural or modified monomer, or a linear oligomer having a bond(s), wherein the natural or modified monomer includes deoxyribonucleotides and ribonucleotides that can be hybridized with a specific nucleotide sequence. Preferably, the probe is present in a single-strand form for the purpose of the maximum efficiency in hybridization. The probe is preferably deoxyribonucleotide.

A nucleotide sequence that is perfectly complementary to the nucleotide sequence may be used as the probe used in the present invention, but nucleotide sequences that are substantially complementary to the nucleotide sequence may be used without obstructing the specific hybridization. Generally, stability of a duplex formed through the hybridization tends to be determined by the consensus of the terminal sequences, and therefore the duplex may be broken down under stringent conditions if the terminal region of the probe having a base complementary to the present nucleotide sequence is not hybridized with the 3'- or 5'-terminus of the probe.

The condition that is suitable for the hybridization may be determined with reference to the context disclosed in Joseph Sambrook, et al., Molecular Cloning, A Laboratory Manual, Cold Spring Harbor Laboratory Press, Cold Spring Harbor, N.Y. (2001) and Haymes, B. D., et al., Nucleic Acid Hybridization, A Practical Approach, IRL Press, Washington, D.C. (1985). The stringent condition used in the hybridization may be determined by adjusting the temperature, the ionic strength (concentration of buffer) and the presence of compounds such as organic solvent. This stringent condition may be differently determined, depending on the sequences to be hybridized.

According to a preferred embodiment, the nucleotide sequence selected from a group consisting of nucleotide sequences as set forth in SEQ ID NO:1 to SEQ ID NO:4 is high-expressed in a patient with high-risk of metastasis of breast cancer, and the nucleotide sequence selected from a group consisting of nucleotide sequences as set forth in SEQ ID NO:5 to SEQ ID NO:9 is low-expressed in a patient with high-risk of metastasis of breast cancer which shows no significant differences in expression levels of the nucleotide sequence selected from a group consisting of nucleotide sequences as set forth in SEQ ID NO:1 to SEQ ID NO:4.

According to the present invention, as a result of function analysis to each gene showing a difference of an expression level between the prognostic groups, the nucleotide sequence selected from a group consisting of nucleotide sequences as set forth in SEQ ID NO:1 to SEQ ID NO:4 is a gene involved in the proliferation of cancer cells, and the nucleotide sequence selected from a group consisting of nucleotide sequences as set forth in SEQ ID NO:5 to SEQ ID NO:9 is a gene involved in the immune response.

In still another aspect of the present invention, there is provided a method for predicting metastasis risk of breast cancer patient comprising measuring the expression of the nucleotide sequence selected from a group consisting of nucleotide sequences as set forth in SEQ ID NO:1 to SEQ ID NO:9. Since the nucleotide sequence and its expression level measurement method used in the present invention is described as above, the common descriptions between them are omitted in order to avoid undue redundancy leading to the complexity of this Specification.

Effects of this Invention

The features and advantages of this invention will be summarized as follows:

(a) The present invention provides a gene selection method for predicting prognosis of cancer, the selected gene for predicting the prognosis of cancer, and a kit and a method for predicting metastasis risk of breast cancer patient using thereof.

(b) The present invention may predict to the patient's prognosis by analyzing for the genetic characteristics of the early stage breast cancer, whereby the present invention may be used to advantage in prognosis diagnosis which may reduce unnecessary anticancer therapy.

BRIEF DESCRIPTION OF THE DRAWINGS

FIG. 1 schematically represents the microarray dataset collected to prognostic gene discovery, development and validation of the model.

FIG. 8 schematically represents results of the prognostic model applying to 3 types of distributions.

FIG. 9a represents that a prognostic index of all patients in the given dataset is divided into four areas and classified into four prognostic groups, and the separation of the observed survival probability of each prognostic group is verified. The observed survival probability is compared with the predicted survival probability. FIG. 9b represents comparison results of the predicted survival probability using the observed survival probability and the prognostic model in overall patients.

FIG. 9c represents results that overall patients are divided into four groups to the most influential p.mean, and the concurrence between the observed survival probability of each group and the predicted survival probability by the prognostic model is verified. FIG. 9d represents results that the concurrence between the observed survival probability and the predicted survival probability at 5-year survival probability is verified.

FIG. 10a represents verification results of determination, FIG. 10b represents verification results of calibration, and FIG. 10c represents verification results of calibration in 5-year survival probability.

FIG. 11a represents verification results of determination, and FIG. 11b represents verification results of calibration. FIG. 11c represents verification results of calibration in at 5-year survival probability.

BEST MODE FOR CARRYING OUT THE INVENTION

Figure 2A:
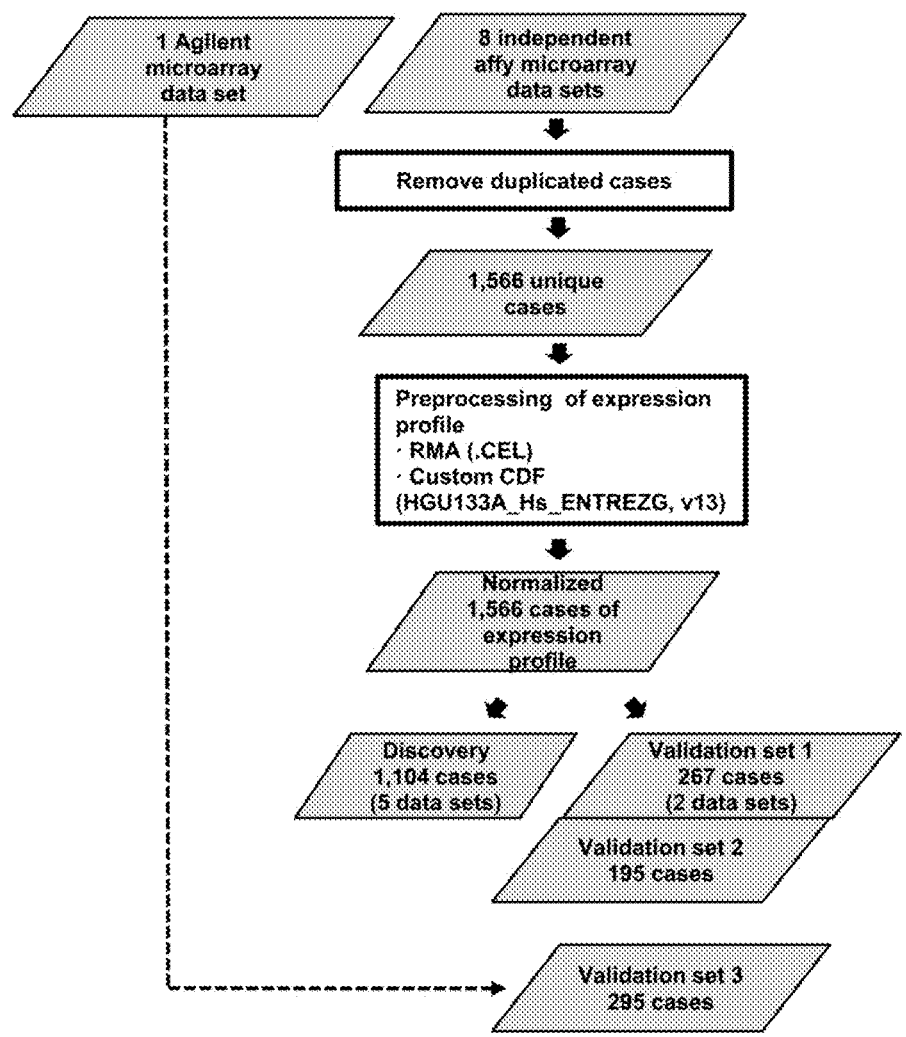
FIG. 2a schematically represents the process of normalization by curation and pre-processing of the microarray data in breast cancer tissue.

The present invention will now be described in further detail by examples. It would be obvious to those skilled in the art that these examples are intended to be more concretely illustrative and the scope of the present invention as set forth in the appended claims is not limited to or by the examples.

EXAMPLES

Experimental Methods
Collection of Expression Profile in the Early Stage Breast Cancer Tissue Expression profiles and clinical information obtained with frozen tissue of the early stage breast cancer were collected from the Gene Expression Omnibus (GEO, at the World Wide Web: ncbi.nlm.nih.gov/geo). Each of total nine independent expression profile sets was consisting of more than 100 samples. It was made to perform prognosis related-researches for the early stage breast cancer patients (2, 4, 9, 10, 13, 25, 32, 33). Eight dataset of them were generated with same platform, Affymetrix® U133A, and last dataset was generated by Agilent Hu25K. Most of them, the patient's clinical information (age, sex, tumor size, state of tumor metastasis and degree of tumor differentiation) and survival information were collected together. Six datasets of eight data sets generated by Affymetrix® U133A information was about distant-metastasis free survival, and last two datasets were about overall survival. Agilent data included survival information for metastasis. Metastasis is the most important event to decide prognosis, and it is determined by the unique characteristics of cancer. In addition, the most frequent patients had metastasis information in the collected data. Based on this metastasis occurrence, survival analysis was performed. From the precise investigation on the expression data and clinical information, about 186 cases turned out to be overlapped in datasets, and the duplicated cases were removed in order to prevent double-counting in statistical analysis such that total 1,861 unique cases were researched. Seven dataset generated with same platform (Affymetrix® U133A) were pooled into a grand dataset, and their raw expression files (.CEL) were combined together by re-preprocessing with RMA algorithm were pooled into a grand dataset, and their raw expression files (.CEL) were normalized with rma (background correction: rma, normalization: quantile, summarization: medianpolish) and ENTREZG version 13 of custom CDF (at the World Wide Web brainarray.mbni.med.umich.edu/Brainarray/) developed by Manhong Dai et al (34). After normalization, the 1-color expression values of the discovery dataset were transformed to 2-color-like values by subtracting the mean of each probe in the discovery dataset. The last dataset generated by Agilent Hu25K was used as another validation set. Separately, five datasets of total eight normalized dataset were hold together to use as the discovery dataset, two datasets were hold together to use a validation dataset 1, and the remaining one was used as a validation dataset 2. Agilent dataset was used as a validation dataset 3.

Definition of Clinical Outcomes and ER Status

To determine the genes showing significantly differential expression between good prognosis group and poor prognosis group, the present inventors defined clinical outcomes in a strict manner to minimize the biases arising from censored survival data. According to the distribution of the distant-meta in the discovery dataset, about 73% of the metastatic patients developed distant-meta within 5 years, and only 7% of them developed distant-meta after 10 years. The present inventors defined good prognosis as 'no distant-meta for more than 10 years', and poor prognosis as 'distant-meta within 5 years'. Following the definitions, 281 patients were assigned to 'good prognosis group', and 217 patients were assigned to 'poor prognosis group'. The median distant-meta survival of the poor prognosis group was 2.4 years. The median distant-meta survival of the good prognosis group was 12.9 years. Estrogen receptor (ER) expression is the most commonly used classification criterion for subtypes of breast cancers. In clinic, pathologist divides into ER+ or ER− by reading the results of ER IHC (immunohistochemistry). To determine the ER status of each sample in the discovery dataset, we used mRNA expression levels of ESR1 on the expression profiles, because about 200 of patients missed ER IHC results and even the available ER IHC results would not be incompatible across independent datasets in which independent decision rules for ER IHC status were applied to.

ROC (region of convergence) analysis was performed using ER IHC results and mRNA expression levels of ESR1 in the patients having ER IHC results. Under the gold standard of ER IHC results, the cutoff for ER status was determined at the point where the accuracy was highest (accuracy=0.88). According to the cutoff, the cases showing higher expression than the cutoff were classified as ER+, and the other cases were classified as ER−. In the discovery dataset, 864 peoples were placed in ER+, and 240 peoples were placed in ER−.

Selection of Prognostic Genes

The present inventors defined good prognosis group as ER+, and poor prognosis group as ER− in the discovery dataset. Following the definitions, 281 patients were assigned to good prognosis group, and 217 patients were assigned to poor prognosis group. Through SAM (Significant Analysis of Microarray), the present inventors selected the genes showing significantly differential expression between two prognosis groups. Using q-value of SAM analysis, 182 of overexpressed genes were selected in good prognosis group, and 120 of overexpressed genes were selected in poor prognosis group. As a result, set of total 302 genes not duplicated has been created. To identify expression patterns of these genes, cluster analysis was performed using PCA (Principal Component Analysis) method. Two principal components were selected, and each cluster was performed by GO function analysis in order to investigate biological functions related to each principal component (Table 1).

TABLE 1

| Gene symbol | Gene name |
| --- | --- |
| Genes overexpressed in poor prognosis group | |
| PRC1 | protein regulator of cytokinesis 1 |
| CCNB2 | cyclin B2 |
| UBE2C | ubiquitin-conjugating enzyme E2C |
| CDC20 | cell division cycle 20 homolog (*S. cerevisiae*) |
| KIF4A | kinesin family member 4A |
| TOP2A | topoisomerase (DNA) II alpha 170 kDa |
| RACGAP1 | Rac GTPase activating protein 1 |
| ASPM | asp (abnormal spindle) homolog, microcephaly associated (*Drosophila*) |
| BUB1B | budding uninhibited by benzimidazoles 1 homolog beta (yeast) |
| CDC45 | cell division cycle 45 homolog (*S. cerevisiae*) |
| PTTG1 | pituitary tumor-transforming 1 |
| CENPF | centromere protein F, 350/400 kDa (mitosin) |
| FOXM1 | forkhead box M1 |
| KIF11 | kinesin family member 11 |
| BLM | Bloom syndrome, RecQ helicase-like |
| ZWINT | ZW10 interactor |
| CDC7 | cell division cycle 7 homolog (*S. cerevisiae*) |
| KIF20A | kinesin family member 20A |
| TRIP13 | thyearoid hormone receptor interactor 13 |
| FANCI | Fanconi anemia, complementation group I |
| MAD2L1 | MAD2 mitotic arrest deficient-like 1 (yeast) |
| MCM2 | minichromosome maintenance complex component 2 |
| RRM2 | ribonucleotide reductase M2 |
| NCAPG | non-SMC condensin I complex, subunit G |
| KIF15 | kinesin family member 15 |
| MLF1IP | MLF1 interacting protein |
| GINS1 | GINS complex subunit 1 (Psf1 homolog) |
| OIP5 | Opa interacting protein 5 |
| NUSAP1 | nucleolar and spindle associated protein 1 |

TABLE 1-continued

| Gene symbol | Gene name |
|---|---|
| ADM | adrenomedullin |
| HMMR | hyaluronan-mediated motility receptor (RHAMM) |
| AURKA | aurora kinase A |
| CCNA2 | cyclin A2 |
| NME1 | non-metastatic cells 1, protein (NM23A) expressed in |
| DLGAP5 | discs, large (*Drosophila*) homolog-associated protein 5 |
| ZDHHC13 | zinc finger, DHHC-type containing 13 |
| HMGB3 | high-mobility group box 3 |
| TMED9 | transmembrane emp24 protein transport domain containing 9 |
| MT1H | metallothionein 1H |
| MMP11 | matrix metallopeptidase 11 (stromelysin 3) |
| TTK | TTK protein kinase |
| ENO2 | enolase 2 (gamma, neuronal) |
| GPR56 | G protein-coupled receptor 56 |
| SPAG5 | sperm associated antigen 5 |
| PBK | PDZ binding kinase |
| MMP1 | matrix metallopeptidase 1 (interstitial collagenase) |
| MST4 | serine/threonine protein kinase MST4 |
| EZH2 | enhancer of zeste homolog 2 (*Drosophila*) |
| CDC25B | cell division cycle 25 homolog B (*S. pombe*) |
| DSCC1 | defective in sister chromatid cohesion 1 homolog (*S. cerevisiae*) |
| CDCA8 | cell division cycle associated 8 |
| CEP55 | centrosomal protein 55 kDa |
| HPSE | heparanase |
| CENPM | centromere protein M |
| CDK1 | cyclin-dependent kinase 1 |
| EYA2 | eyes absent homolog 2 (*Drosophila*) |
| TMSB15B | thymosin beta 15B |
| GGH | gamma-glutamyl hydrolase (conjugase, folylpolygammaglutamyl hydrolase) |
| PSMD3 | proteasome (prosome, macropain) 26S subunit, non-ATPase, 3 |
| FGD1 | FYVE, RhoGEF and PH domain containing 1 |
| ASF1B | ASF1 anti-silencing function 1 homolog B (*S. cerevisiae*) |
| SPAG16 | sperm associated antigen 16 |
| SMC4 | structural maintenance of chromosomes 4 |
| C11orf80 | chromosome 11 open reading frame 80 |
| LSM1 | LSM1 homolog, U6 small nuclear RNA associated (*S. cerevisiae*) |
| PMEPA1 | prostate transmembrane protein, androgen induced 1 |
| CDKN3 | cyclin-dependent kinase inhibitor 3 |
| TOPBP1 | topoisomerase (DNA) II binding protein 1 |
| CCT5 | chaperonin containing TCP1, subunit 5 (epsilon) |
| RAD51AP1 | RAD51 associated protein 1 |
| GPSM2 | G-protein signaling modulator 2 |
| LIG1 | ligase I, DNA, ATP-dependent |
| NMU | neuromedin U |
| KIAA1199 | KIAA1199 |
| DTL | denticleless homolog (*Drosophila*) |
| KIF2C | kinesin family member 2C |
| WDR45L | WDR45-like |
| SLC16A3 | solute carrier family 16, member 3 (monocarboxylic acid transporter 4) |
| MT1F | metallothionein 1F |
| C18orf8 | chromosome 18 open reading frame 8 |
| STMN1 | stathmin 1 |
| HSPA1A | heat shock 70 kDa protein 1A |
| PUS7 | pseudouridylate synthase 7 homolog (*S. cerevisiae*) |
| GPR172A | G protein-coupled receptor 172A |
| SCRN1 | secernin 1 |
| AURKB | aurora kinase B |
| GALNT14 | UDP-N-acetyl-alpha-D-galactosamine: polypeptide N-acetylgalactosaminyltransferase 14 (GalNAc-T14) |
| SPP1 | secreted phosphoprotein 1 |
| NUP107 | nucleoporin 107 kDa |
| C21orf45 | chromosome 21 open reading frame 45 |
| CTPS | CTP synthase |
| GINS2 | GINS complex subunit 2 (Psf2 homolog) |
| CCNE2 | cyclin E2 |
| GSDMB | gasdermin B |
| RIPK4 | receptor-interacting serine-threonine kinase 4 |
| TMSB15A | thymosin beta 15a |
| MYBL1 | v-myb myeloblastosis viral oncogene homolog (avian)-like 1 |
| KIF14 | kinesin family member 14 |
| TK1 | thymidine kinase 1, soluble |
| ABCC10 | ATP-binding cassette, sub-family C (CFTR/MRP), member 10 |
| CIAPIN1 | cytokine induced apoptosis inhibitor 1 |
| TXNRD1 | thioredoxin reductase 1 |
| GLDC | glycine dehydrogenase (decarboxylating) |
| SAP30 | Sin3A-associated protein, 30 kDa |
| TYMS | thymidylate synthetase |

TABLE 1-continued

| Gene symbol | Gene name |
|---|---|
| LLGL2 | lethal giant larvae homolog 2 (*Drosophila*) |
| EPN3 | epsin 3 |
| DONSON | downstream neighbor of SON |
| NCAPG2 | non-SMC condensin II complex, subunit G2 |
| C1orf135 | chromosome 1 open reading frame 135 |
| CDCA3 | cell division cycle associated 3 |
| MKI67 | antigen identified by monoclonal antibody Ki-67 |
| F12 | coagulation factor XII (Hageman factor) |
| ELMO3 | engulfment and cell motility 3 |
| TMEM132A | transmembrane protein 132A |
| SCRIB | scribbled homolog (*Drosophila*) |
| EXO1 | exonuclease 1 |
| AP3M2 | adaptor-related protein complex 3, mu 2 subunit |
| CYCS | cytochrome c, somatic |
| NPM3 | nucleophosmin/nucleoplasmin 3 |
| Genes overexpressed in good prognosis group | |
| TRBV20-1 | T cell receptor beta variable 20-1 |
| CCL19 | chemokine (C-C motif) ligand 19 |
| CD52 | CD52 molecule |
| SRGN | serglycin |
| CD3D | CD3d molecule, delta (CD3-TCR complex) |
| IGJ | immunoglobulin J polypeptide, linker protein for immunoglobulin alpha and mu polypeptides |
| HLA-DRA | major histocompatibility complex, class II, DR alpha |
| LOC91316 | glucuronidase, beta/immunoglobulin lambda-like polypeptide 1 pseudogene |
| IGF1 | insulin-like growth factor 1 (somatomedin C) |
| CYBRD1 | cytochrome b reductase 1 |
| TMC5 | transmembrane channel-like 5 |
| ALDH1A1 | aldehyde dehydrogenase 1 family, member A1 |
| OGN | osteoglycin |
| PDCD4 | programmed cell death 4 (neoplastic transformation inhibitor) |
| FRZB | frizzled-related protein |
| CX3CR1 | chemokine (C-X3-C motif) receptor 1 |
| IGFBP6 | insulin-like growth factor binding protein 6 |
| GLA | galactosidase, alpha |
| LOC96610 | BMS1 homolog, ribosome assembly protein (yeast) pseudogene |
| IGLL3 | immunoglobulin lambda-like polypeptide 3 |
| ITPR1 | inositol 1,4,5-triphosphate receptor, type 1 |
| SERPINA1 | serpin peptidase inhibitor, clade A (alpha-1 antiproteinase, antitrypsin), member 1 |
| EPHX2 | epoxide hydrolase 2, cytoplasmic |
| MFAP4 | microfibrillar-associated protein 4 |
| RNASET2 | ribonuclease T2 |
| CCNG1 | cyclin G1 |
| FBLN5 | fibulin 5 |
| SORBS2 | sorbin and SH3 domain containing 2 |
| CCBL2 | cysteine conjugate-beta lyase 2 |
| BTN3A2 | butyearophilin, subfamily 3, member A2 |
| TFAP2B | transcription factor AP-2 beta (activating enhancer binding protein 2 beta) |
| LTF | lactotransferrin |
| ITM2A | integral membrane protein 2A |
| HLA-DPB1 | major histocompatibility complex, class II, DP beta 1 |
| HLA-DMA | major histocompatibility complex, class II, DM alpha |
| RPL3 | ribosomal protein L3 |
| LOC100130100 | similar to hCG26659 |
| FAM129A | family with sequence similarity 129, member A |
| ELOVL5 | ELOVL family member 5, elongation of long chain fatty acids (FEN1/Elo2, SUR4/Elo3-like, yeast) |
| GBP2 | guanylate binding protein 2, interferon-inducible |
| RARRES3 | retinoic acid receptor responder (tazarotene induced) 3 |
| GOLM1 | golgi membrane protein 1 |
| RTN1 | reticulon 1 |
| ICAM3 | intercellular adhesion molecule 3 |
| LAMA2 | laminin, alpha 2 |
| CXCL13 | chemokine (C-X-C motif) ligand 13 |
| ZCCHC24 | zinc finger, CCHC domain containing 24 |
| CD37 | CD37 molecule |
| VTCN1 | V-set domain containing T cell activation inhibitor 1 |
| PYCARD | PYD and CARD domain containing |
| CORO1A | coronin, actin binding protein, 1A |
| SH3BGRL | SH3 domain binding glutamic acid-rich protein like |
| TPSAB1 | tryptase alpha/beta 1 |
| TNFSF10 | tumor necrosis factor (ligand) superfamily, member 10 |
| ACSF2 | acyl-CoA synthetase family member 2 |
| TGFBR2 | transforming growth factor, beta receptor II (70/80 kDa) |

TABLE 1-continued

| Gene symbol | Gene name |
|---|---|
| DUSP4 | dual specificity phosphatase 4 |
| ARHGDIB | Rho GDP dissociation inhibitor (GDI) beta |
| TMPRSS3 | transmembrane protease, serine 3 |
| DCN | decorin |
| LRIG1 | leucine-rich repeats and immunoglobulin-like domains 1 |
| FMOD | fibromodulin |
| ZNF423 | zinc finger protein 423 |
| SQRDL | sulfide quinone reductase-like (yeast) |
| TPST2 | tyearosylprotein sulfotransferase 2 |
| CD44 | CD44 molecule (Indian blood group) |
| MREG | melanoregulin |
| GIMAP6 | GTPase, IMAP family member 6 |
| GJA1 | gap junction protein, alpha 1, 43 kDa |
| IFITM3 | interferon induced transmembrane protein 3 (1-8U) |
| BTG2 | BTG family, member 2 |
| PIP | prolactin-induced protein |
| RPS9 | ribosomal protein S9 |
| HLA-DPA1 | major histocompatibility complex, class II, DP alpha 1 |
| IMPDH2 | IMP (inosine 5'-monophosphate) dehydrogenase 2 |
| TNFRSF17 | tumor necrosis factor receptor superfamily, member 17 |
| C14orf139 | chromosome 14 open reading frame 139 |
| SPRY2 | sprouty homolog 2 (*Drosophila*) |
| XBP1 | X-box binding protein 1 |
| THYN1 | thymocyte nuclear protein 1 |
| APOD | apolipoprotein D |
| C10orf116 | chromosome 10 open reading frame 116 |
| VAV3 | vav 3 guanine nucleotide exchange factor |
| FAS | Fas (TNF receptor superfamily, member 6) |
| MYBPC1 | myosin binding protein C, slow type |
| CFB | complement factor B |
| TRIM22 | tripartite motif-containing 22 |
| ARID5B | AT rich interactive domain 5B (MRF1-like) |
| PTGDS | prostaglandin D2 synthase 21 kDa (brain) |
| TGFBR3 | transforming growth factor, beta receptor III |
| TNFAIP8 | tumor necrosis factor, alpha-induced protein 8 |
| SEMA3C | sema domain, immunoglobulin domain (Ig), short basic domain, secreted, (semaphorin) 3C |
| TMEM135 | transmembrane protein 135 |
| ARHGEF3 | Rho guanine nucleotide exchange factor (GEF) 3 |
| PTGER4 | prostaglandin E receptor 4 (subtype EP4) |
| ABCA8 | ATP-binding cassette, sub-family A (ABC1), member 8 |
| ICAM2 | intercellular adhesion molecule 2 |
| HLA-DQB1 | major histocompatibility complex, class II, DQ beta 1 |
| HSPA2 | heat shock 70 kDa protein 2 |
| CD27 | CD27 molecule |
| ARMCX1 | armadillo repeat containing, X-linked 1 |
| POU2AF1 | POU class 2 associating factor 1 |
| IGBP1 | immunoglobulin (CD79A) binding protein 1 |
| PDE4B | phosphodiesterase 4B, cAMP-specific |
| ADH1B | alcohol dehydrogenase 1B (class I), beta polypeptide |
| WLS | wntless homolog (*Drosophila*) |
| SUCLG2 | succinate-CoA ligase, GDP-forming, beta subunit |
| PGR | progesterone receptor |
| STARD13 | StAR-related lipid transfer (START) domain containing 13 |
| SORL1 | sortilin-related receptor, L(DLR class) A repeats-containing |
| ATP1B1 | ATPase, Na+/K+ transporting, beta 1 polypeptide |
| IFT46 | intraflagellar transport 46 homolog (*Chlamydomonas*) |
| SIK3 | SIK family kinase 3 |
| LIPT1 | lipoyltransferase 1 |
| OMD | osteomodulin |
| HBB | hemoglobin, beta |
| C3 | complement component 3 |
| FGL2 | fibrinogen-like 2 |
| PECI | peroxisomal D3,D2-enoyl-CoA isomerase |
| RAC2 | ras-related C3 botulinum toxin substrate 2 (rho family, small GTP binding protein Rac2) |
| PDZRN3 | PDZ domain containing ring finger 3 |
| CXCL12 | chemokine (C-X-C motif) ligand 12 |
| DPYD | dihydropyearimidine dehydrogenase |
| TXNDC15 | thioredoxin domain containing 15 |
| STOM | stomatin |
| EMCN | endomucin |
| SCGB2A2 | secretoglobin, family 2A, member 2 |
| FAM176B | family with sequence similarity 176, member B |
| HIGD1A | HIG1 hypoxia inducible domain family, member 1A |
| ACSL5 | acyl-CoA synthetase long-chain family member 5 |
| RPS24 | ribosomal protein S24 |
| RGS10 | regulator of G-protein signaling 10 |

TABLE 1-continued

| Gene symbol | Gene name |
|---|---|
| RAI2 | retinoic acid induced 2 |
| CNN3 | calponin 3, acidic |
| FBXW4 | F-box and WD repeat domain containing 4 |
| SEPP1 | selenoprotein P, plasma, 1 |
| SLC44A4 | solute carrier family 44, member 4 |
| MGP | matrix Gla protein |
| ABCD3 | ATP-binding cassette, sub-family D (ALD), member 3 |
| SETBP1 | SET binding protein 1 |
| APOBEC3G | apolipoprotein B mRNA editing enzyme, catalytic polypeptide-like 3G |
| LCP2 | lymphocyte cytosolic protein 2 (SH2 domain containing leukocyte protein of 76 kDa) |
| HLA-DRB1 | major histocompatibility complex, class II, DR beta 1 |
| SCUBE2 | signal peptide, CUB domain, EGF-like 2 |
| DEPDC6 | DEP domain containing 6 |
| RPL15 | ribosomal protein L15 |
| SH3BP4 | SH3-domain binding protein 4 |
| MSX2 | msh homeobox 2 |
| CLU | clusterin |
| DPT | dermatopontin |
| ZNF238 | zinc finger protein 238 |
| HBP1 | HMG-box transcription factor 1 |
| GSTK1 | glutathione S-transferase kappa 1 |
| ZBTB16 | zinc finger and BTB domain containing 16 |
| CCDC69 | coiled-coil domain containing 69 |
| ALDH2 | aldehyde dehydrogenase 2 family (mitochondrial) |
| SLC1A1 | solute carrier family 1 (neuronal/epithelial high affinity glutamate transporter, system Xag), member 1 |
| ARMCX2 | armadillo repeat containing, X-linked 2 |
| HMGCS2 | 3-hydroxy-3-methylglutaryl-CoA synthase 2 (mitochondrial) |
| TSPAN3 | tetraspanin 3 |
| FTO | fat mass and obesity associated |
| PON2 | paraoxonase 2 |
| C16orf62 | chromosome 16 open reading frame 62 |
| QDPR | quinoid dihydropteridine reductase |
| LRP2 | low density lipoprotein receptor-related protein 2 |
| PSMB8 | proteasome (prosome, macropain) subunit, beta type, 8 (large multifunctional peptidase 7) |
| HCLS1 | hematopoietic cell-specific Lyn substrate 1 |
| FXYD1 | FXYD domain containing ion transport regulator 1 |
| OAT | ornithine aminotransferase |
| SLC38A1 | solute carrier family 38, member 1 |
| MAOA | monoamine oxidase A |
| LPL | lipoprotein lipase |
| C10orf57 | chromosome 10 open reading frame 57 |
| SPARCL1 | SPARC-like 1 (hevin) |
| ERAP2 | endoplasmic reticulum aminopeptidase 2 |
| PDGFRL | platelet-derived growth factor receptor-like |
| RBP4 | retinol binding protein 4, plasma |
| LRRC17 | leucine rich repeat containing 17 |
| LHFP | lipoma HMGIC fusion partner |
| BLNK | B-cell linker |
| HBA2 | hemoglobin, alpha 2 |
| CST7 | cystatin F (leukocystatin) |

As a result of GO analysis, it is determined that the principal component 1 was concentrated in the proliferation, and the principal component 2 was concentrated in the immune response. In genes belonging to the two principal components involved in the proliferation and the immune response, 4 genes and 5 genes showing the highest expression level between two prognosis groups were selected respectively. Each gene set is named as p-gene representing expression patterns of the proliferation and i-gene representing expression patterns of the immune response.

Development of a Prognostic Model

The present inventors performed regression analysis in which expression levels of p-gene and i-gene were covariates using the accelerated failure time (AFT) models based on various parametric distributions. 4 p-genes were converted to p.mean, and 5 i-genes to i.mean by calculating the average per patient to apply. AFT models are specified as $$T_i = T_0 \exp(\beta_1 \chi_1 + \beta_2 \chi_2 + \ldots + \beta_q \chi_q) \cdot \varepsilon_i \quad (1)$$

wherein $T_i$ is the survival time of the i th object, $T_o$ is the baseline survival time, $\chi_j$ is the vector of the covariates (j=1, 2, ..., q), β is the coefficient of the corresponding covariates and E is the error. Since the covariates synergistically influence the baseline survival time in this model, it is called the accelerated failure time (AFT) model in the industry frequently used this. Synergistic effect on the survival time $\Phi = \beta_1 \chi_1 + \beta_2 \chi_2 + \ldots + \beta_q \chi_q$ is called the acceleration factor.

Where the natural logarithm in Equation (1) is calculated, AFT models are specified as $$\log T_i = \log T_0 + \beta_1 \chi_1 + \beta_2 \chi_2 + \ldots + \beta_q \chi_q + \varepsilon^* \quad (2)$$

whereby AFT model has the same form as the general linear regression model.

However, since the dependent variable log T not only normally distributes but also there must always exist censored cases in survival analysis data, Equation (2) cannot be processed as the linear regression model. It is cumbersome to process practical statistics because distribution in $\varepsilon^*$ of Equation (2) may differ depending on each dataset. To overcome this, log T0 and ε* are modified and expressed by as follows.

$$\log T = \beta_0 + \beta_1 \chi_1 + \beta_2 \chi_2 + \ldots + \beta_q \chi_q + \sigma W \qquad (3)$$

wherein W follows in the distribution of Log T, and the distribution is fixed as the value of the standardized distribution. The scale parameter σ is a constant, and its value is determined by the dataset. The present inventors selected the best model from a set of candidate prognostic models by fitting them to the Weibull, loglogistic and lognormal distributions. The shape of hazard function was explored by fitting the hazard rate calculated from the life table of the discovery dataset to risk distribution for AFT model. Since the hazard function obtained by the life table shows a form of unimodal, it was predicted that the Weibull, loglogistic and lognormal distributions would appropriate. The final model was chosen considering Akaike's information criterion (AIC) and the R square (R2).

Validation of the Prognostic Model

The performance of the prognostic model was assessed in terms of 'calibration' and 'discrimination'. 'Calibration' is the degree of correspondence between the estimated probability produced by the model and the actual observed probability. 'Discrimination' is the ability of the model to correctly separate the subjects into different groups. Calibration was evaluated with the calibration curves plotted as observed versus predicted survival. 'Predicted' means predicted survival probability by a model, and 'observed' refers to the corresponding Kaplan-Meier survival estimate. For each patient in the data set, the model was used to predict survival probabilities for all time points up to the date of the occurrence of distant-meta. The predicted survival probabilities were averaged over all cases in the sub set at each time point (from 0 to 25 by 0.1) to give a survival curve representative of the sub group. Using this method allows comparison of observed and predicted survival in groups of patients. Together comparison of survival probability for the overall survival time, the survival probability for 5-year was also compared. A prognostic index of all patients in the given dataset was divided into four areas, and survival probabilities of patients belonging to each area were compared with KM graph to discriminate. The prognostic index is the dependent variable in the model. The more the KM graph to the four prognostic groups is clearly divided, the better model has discrimination power.

'Calibration' and 'determination' for discovery dataset and three independent validation datasets was investigated.

All statistical analyses were performed using the open source statistical language R with the packages below.

affy: preprocessing of .CEL files using rma algorithm samr: mining of the genes showing differentially expressed between two prognosis groups GOstats: GO analysis for the identified expression patterns KMsurv: creating of a life table of the discovery dataset rms: fitting prognostic models to various parametric distribution and calibration of the model using AFT model Result Selection of the p-Genes and i-Genes Five independent breast cancer datasets were pooled into a grand discovery data set consisted of 1,072 unique cases. All patients did not receive chemotherapy, and they have no metastasis of axillary lymph node (N0 or N−), or have the early stage breast cancer (1st stage or 2nd stage). Among them, 1072 peoples with information about metastasis were performed to target statistical analysis. To search for genes associated with prognosis, the present inventors divided into good prognosis as 'no distant-meta for more than 10 years' and poor prognosis as 'distant-meta within 5 years' to compare expression profiles. 182 of overexpressed genes were selected in good prognosis group, and 120 of overexpressed genes were selected in poor prognosis group (FDR<0.001). PCA (Principal Component Analysis) were performed to the selected 302 genes. GO function analysis was performed to principal Component 1 and 2. It is determined that the principal component 1 was concentrated in the proliferation, and the principal component 2 was concentrated in the immune response. In genes belonging to the two principal components involved in the proliferation and the immune response, 4 genes and 5 genes showing the highest expression level between two prognosis groups were selected respectively. Based on this, the present inventors selected 4 genes from principal component 1 (proliferation) and 5 genes from principal component 2 (immune response) to develop a prognostic model.

The 9 genes were selected genes that are not only associated with prognosis, but also have the largest expression difference between the groups. Each gene is named as p-gene representing expression patterns of the proliferation and i-gene representing expression patterns of the immune response.

Comparison on ER+ Breast Cancer and ER− Breast Cancer

Occurrence of estrogen receptor (ER) expression is known to be closely related to generation and development of breast cancer. Two functions (i.e., proliferation and immune response) representing the genes selected with regard to the prognosis are interesting functions in mechanism of cancer. Using the expression levels of the p-genes and i-genes as a measure of biological activity, we compared ER+ tumors and ER− tumors in terms of the activity of proliferation and immune response. We stratified the pooled data set into 3 subgroups according to the expression levels of either the p-genes or the i-genes, and the subgroups represented 3-steps intensity of proliferation or immune response (p1, p2, p3 or i1, i2, i3). p1 was a group of the lowest expression level of the p-gene and it was considered to be the slowest proliferation. p3 was a group of the highest expression levels of the p-genes and it was considered to be the most active proliferation. p2 showing a moderate expression level of the p-gene was considered to be a moderate proliferation. i1 was a group of the lowest expression level of the i-gene and it was considered to be the weakest immune response. i3 was a group of the highest expression levels of the i-genes and it was considered to be the strongest immune response. i2 showing a moderate expression level of the i-gene was considered to be a moderate immune response.

Figure 2B:
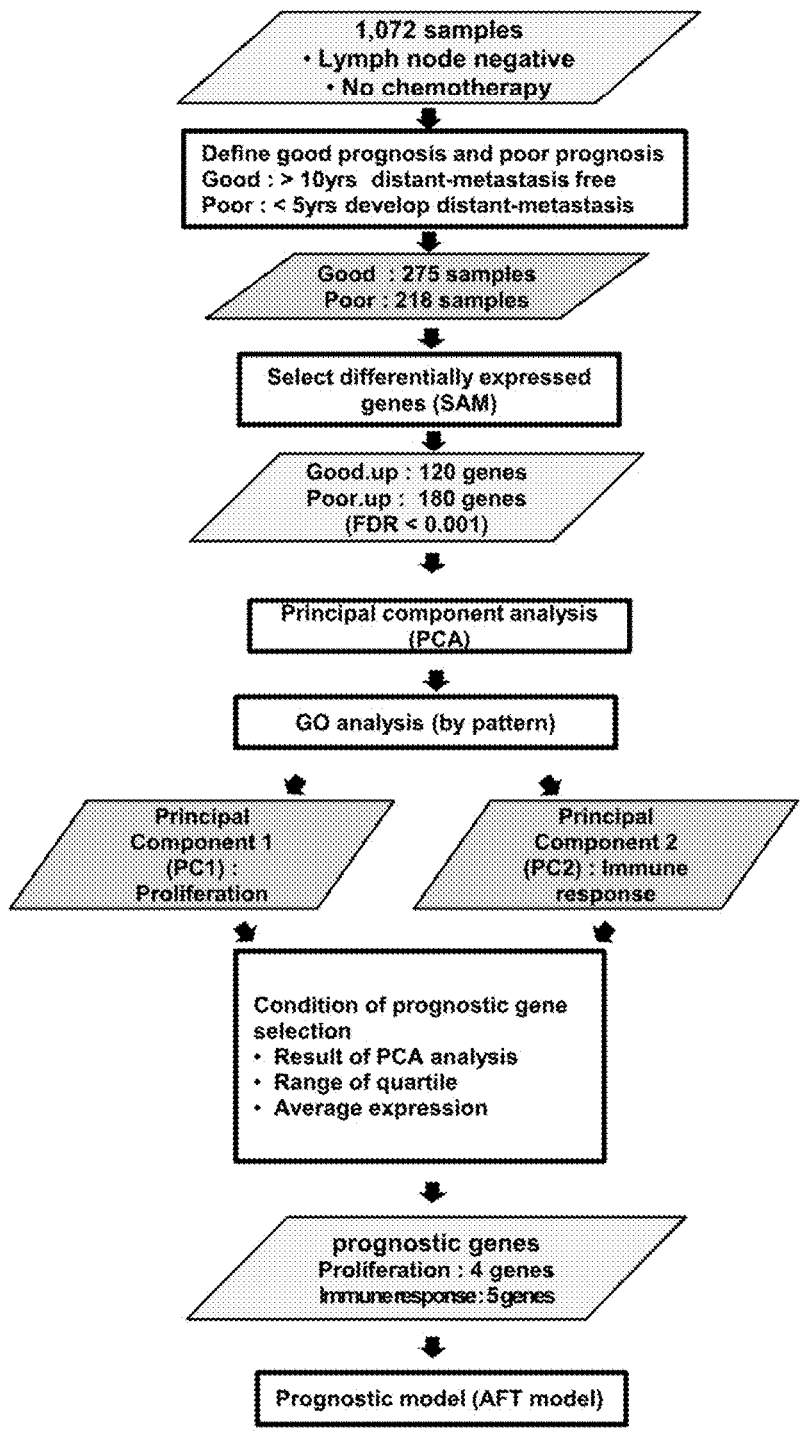
FIG. 2b schematically represents the process for developing prognostic gene in the discovery dataset.
Figure 3:
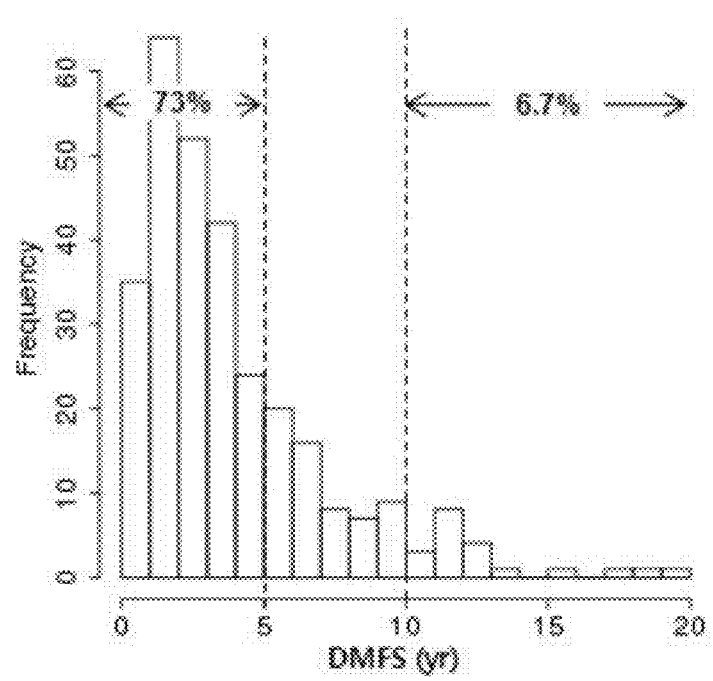
FIG. 3 schematically represents the distribution of occurrence time of metastases into other organs in the discovery dataset in patients.
Figure 4A:
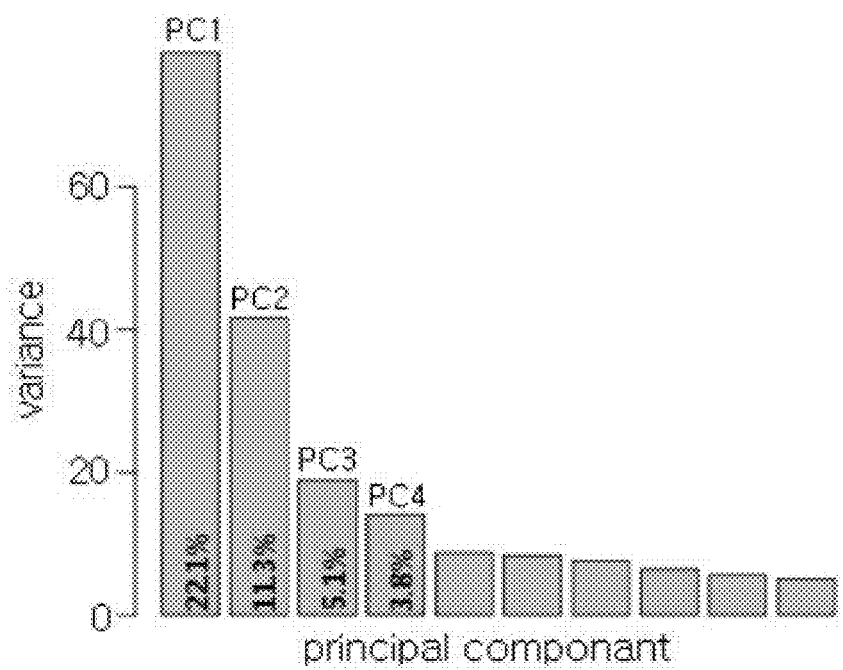
FIG. 4a represents a result of principal component analysis for 302 genes showing significantly differential expression levels between prognostic groups.
Figure 4B:
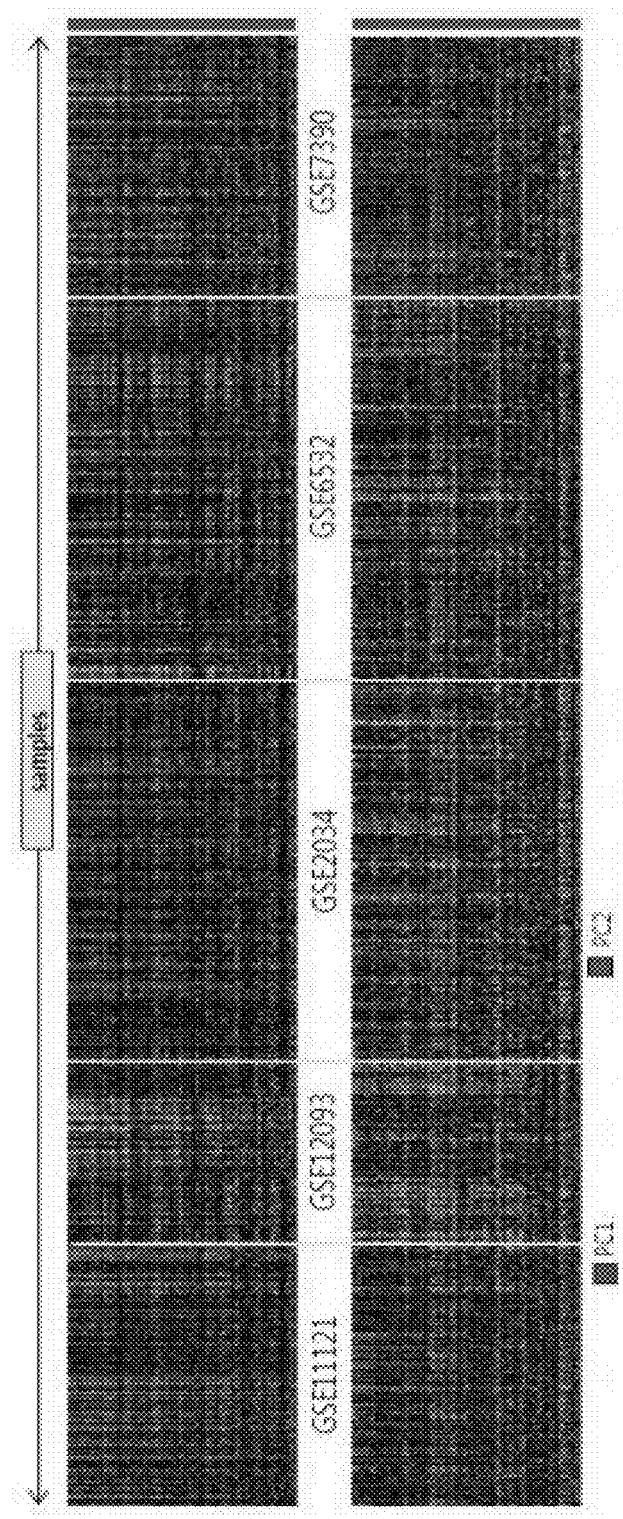
FIG. 4b represents expression level patterns to 70 genes highly correlated with principal component 1 and 2, respectively.
Figure 5A:
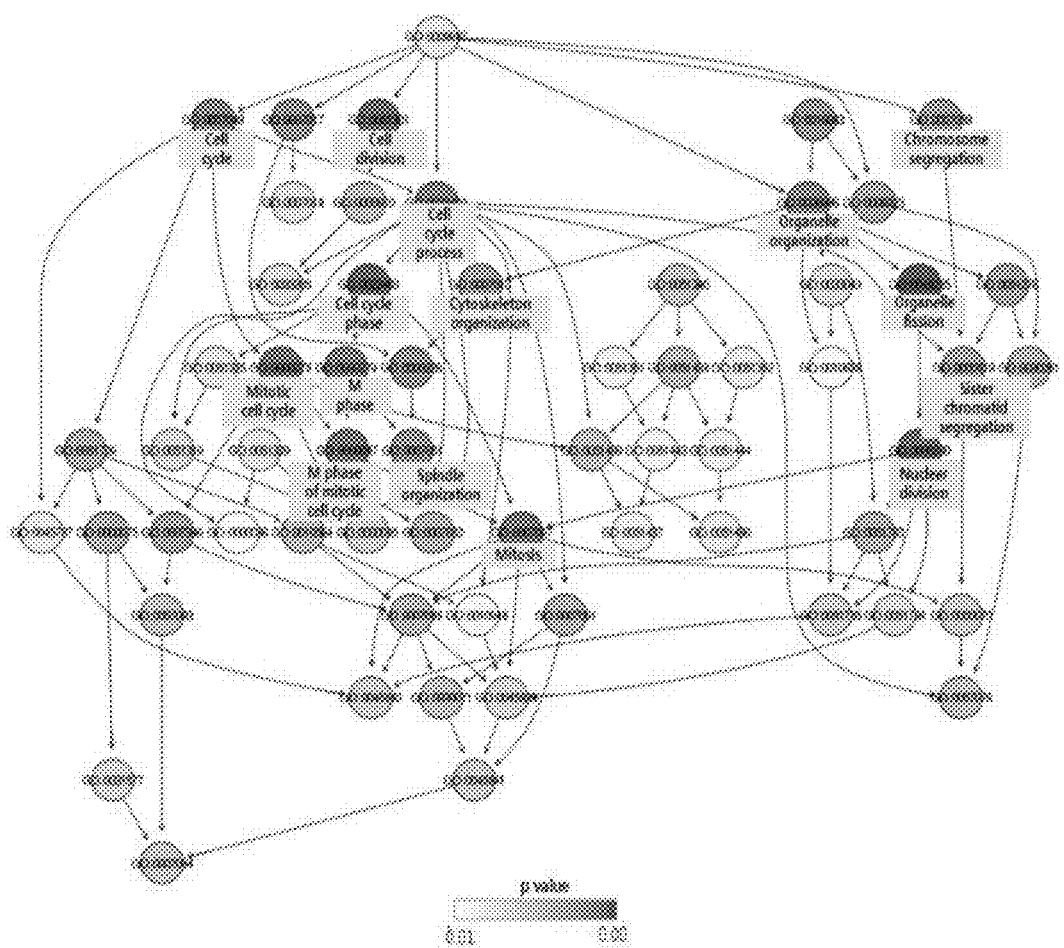
FIG. 5a represents a result of GO function analysis to 70 genes highly correlated with principal component 1.
Figure 5B:
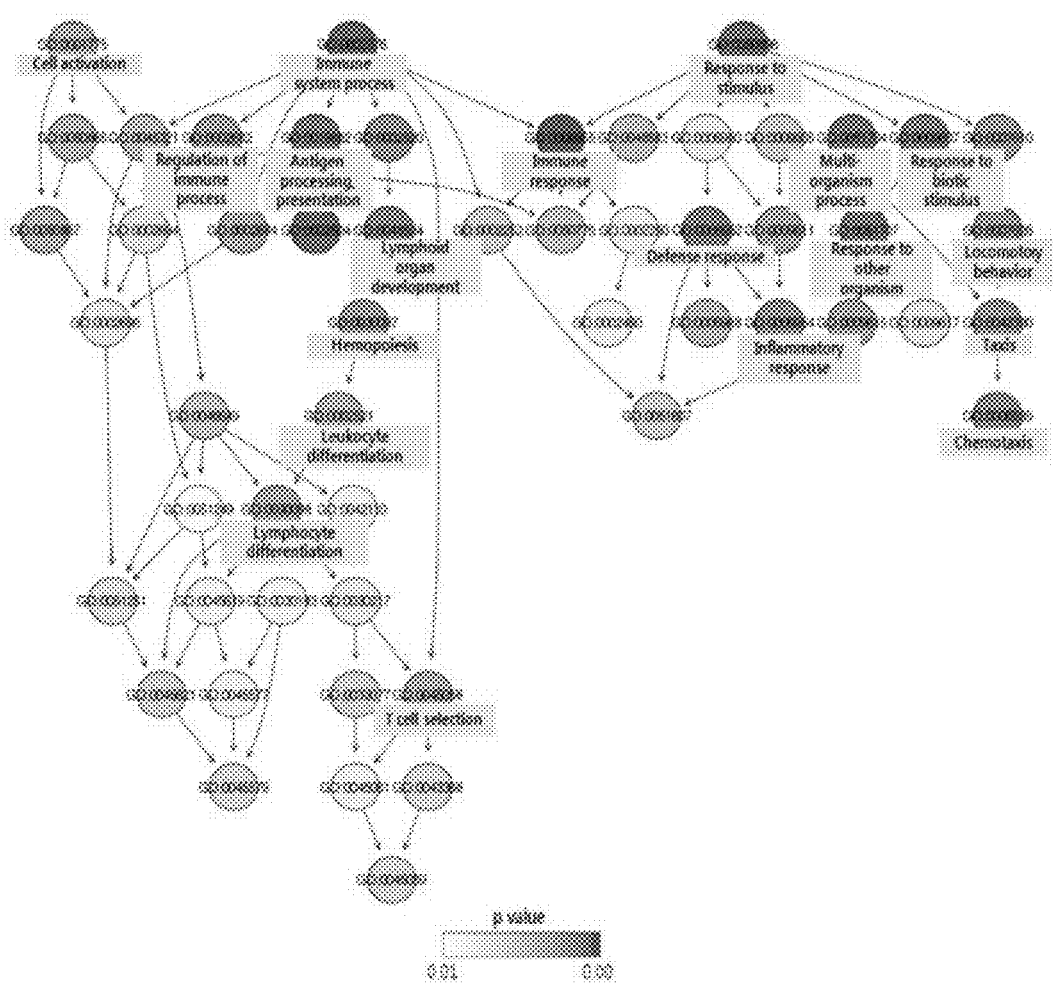
FIG. 5b represents a result of GO function analysis to 70 genes highly correlated with principal component 2.
Figure 6A:
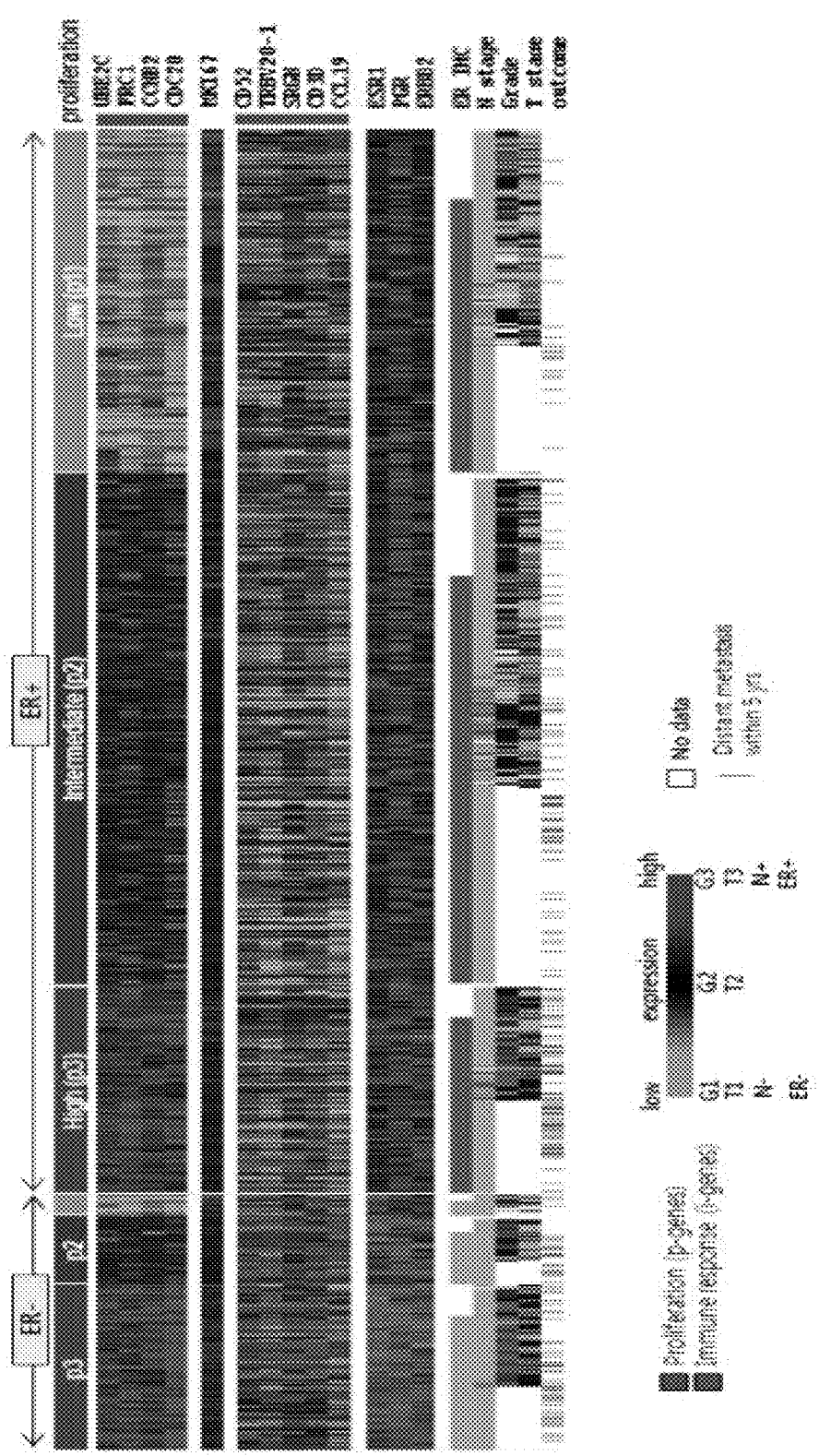
FIG. 6a schematically represents results of comparison on the degree of the proliferation and the immune response by classifying breast cancer into ER+ and ER− using the selected prognostic genes.
Figure 6B:
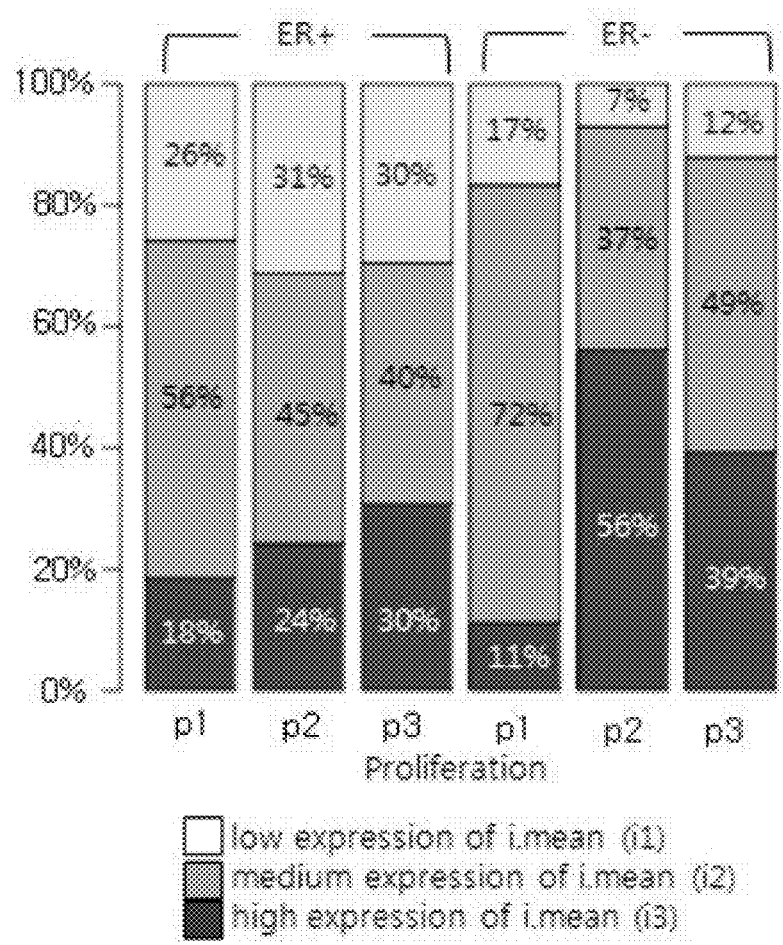
FIG. 6b represents results that as the proliferation is increased, the immune response is increased where the degree of the proliferation and the immune response are respectively divided into three sections.
Figure 7A:
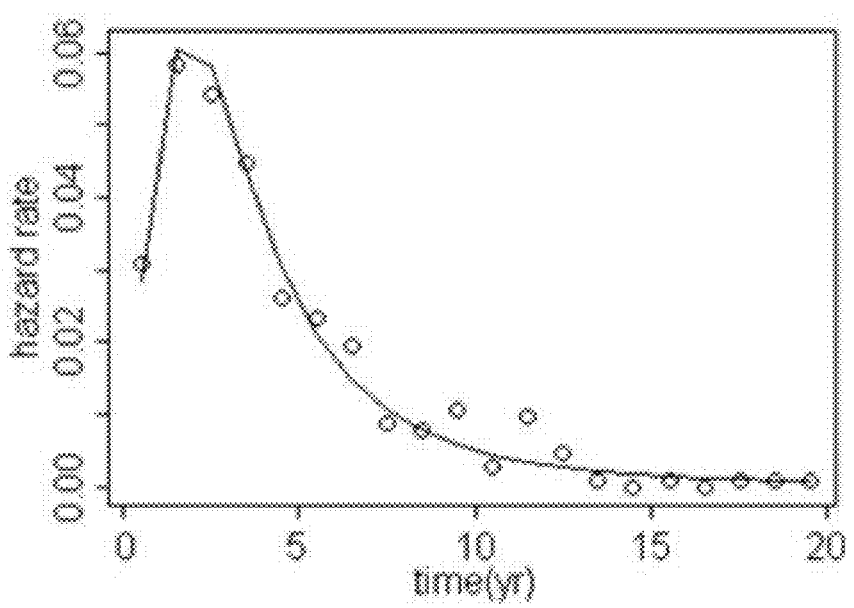
FIG. 7a schematically represents the shape of hazard function calculated using life table of the discovery dataset.
Figure 7B:
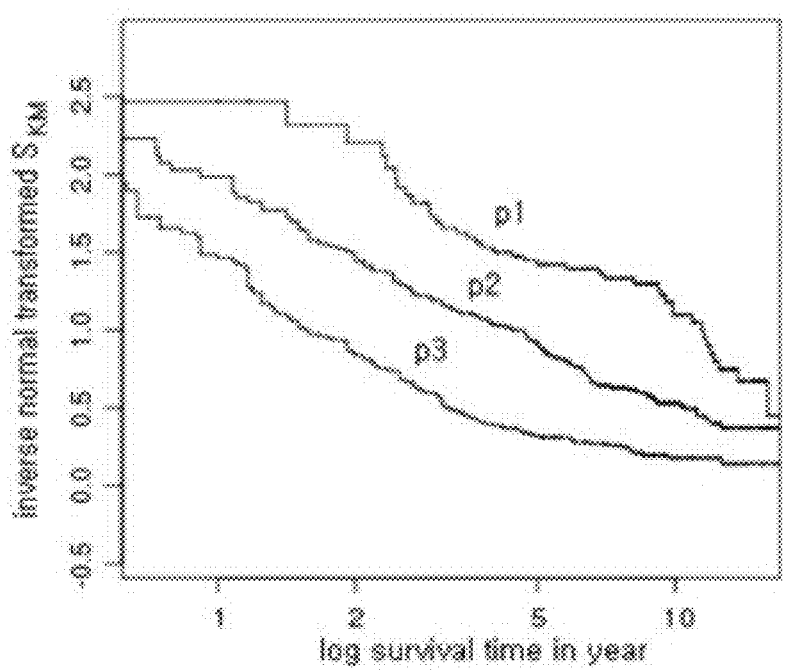
FIG. 7b schematically represents the graph showing linearity and parallelism of the survival probability in lognormal distribution.
Figure 9A:
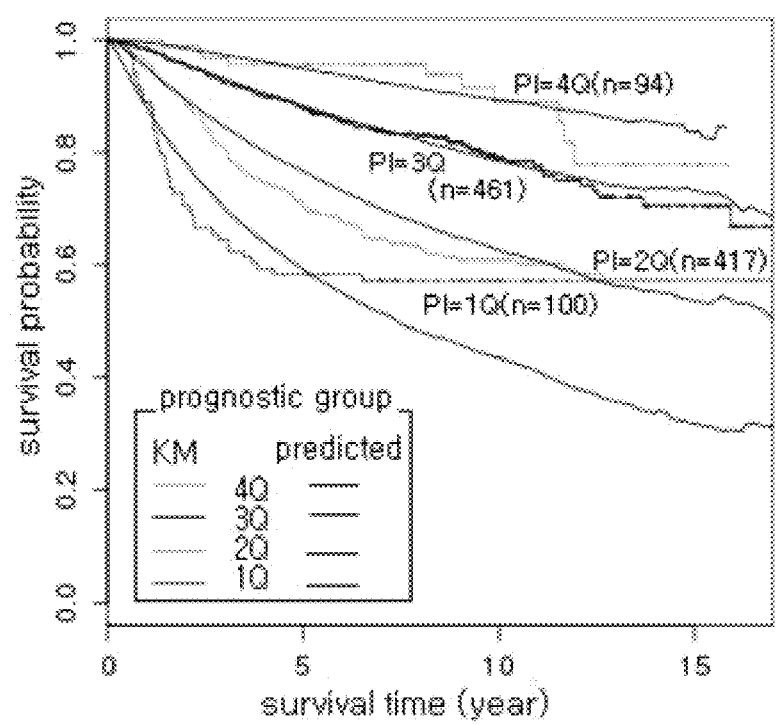
FIGS. 9a-9d represent verification results of the prognostic model in discovery data set.
Figure 9B:
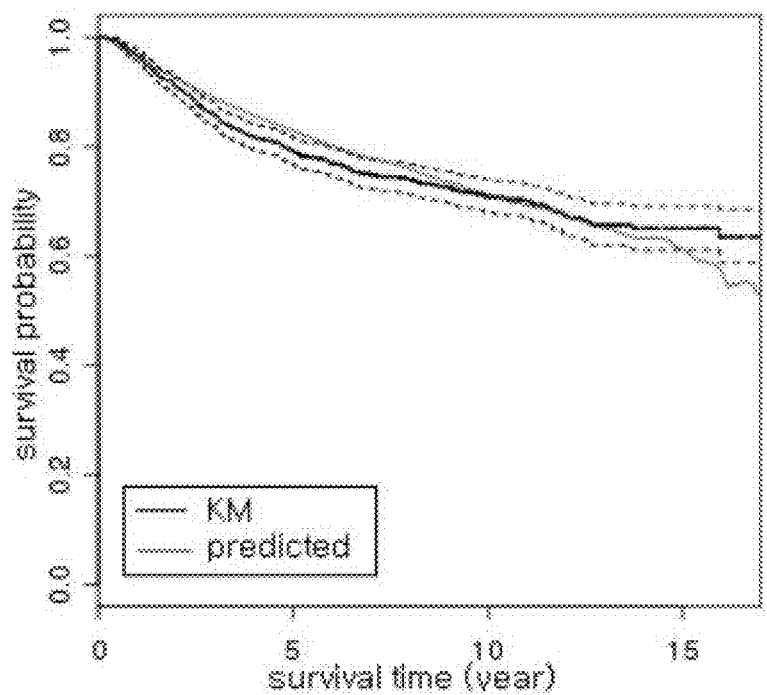
Figure 9C:
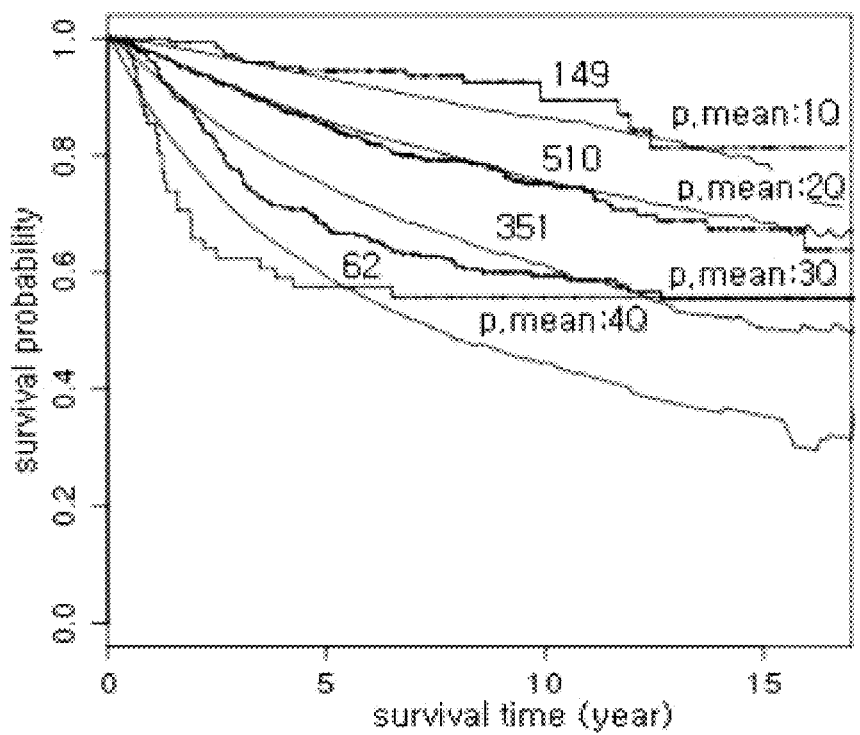
Figure 9D:
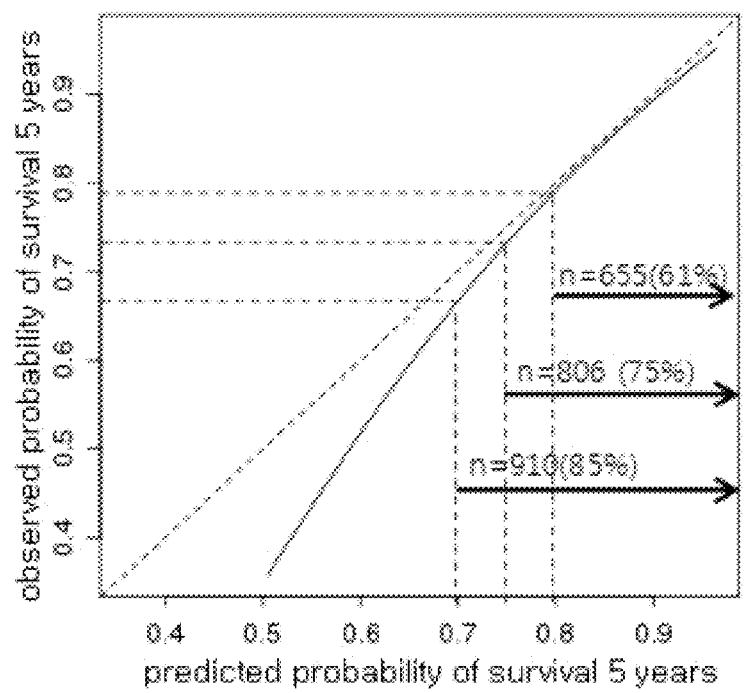
Figure 10A:
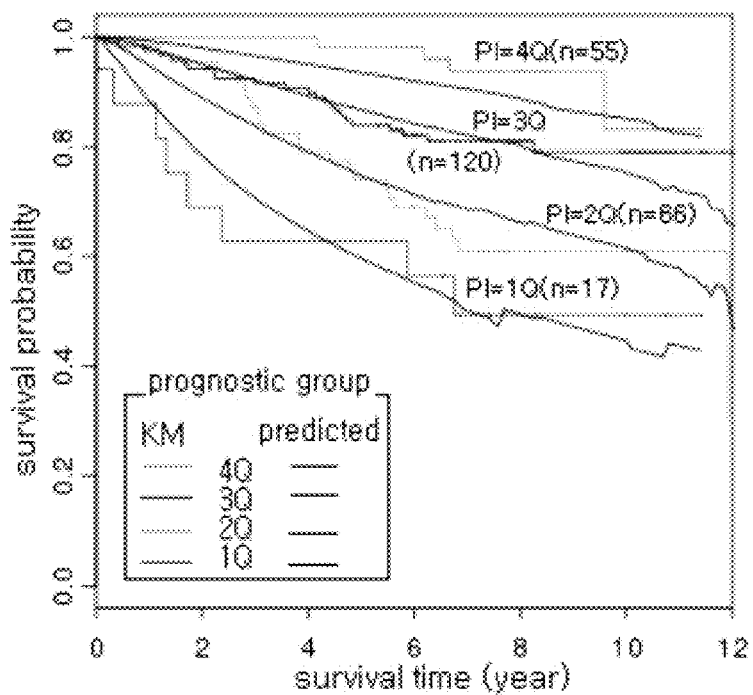
FIGS. 10a-10c represent verification results of the prognostic model in the validation set 1 and it is same verification method as the discovery set.
Figure 10B:
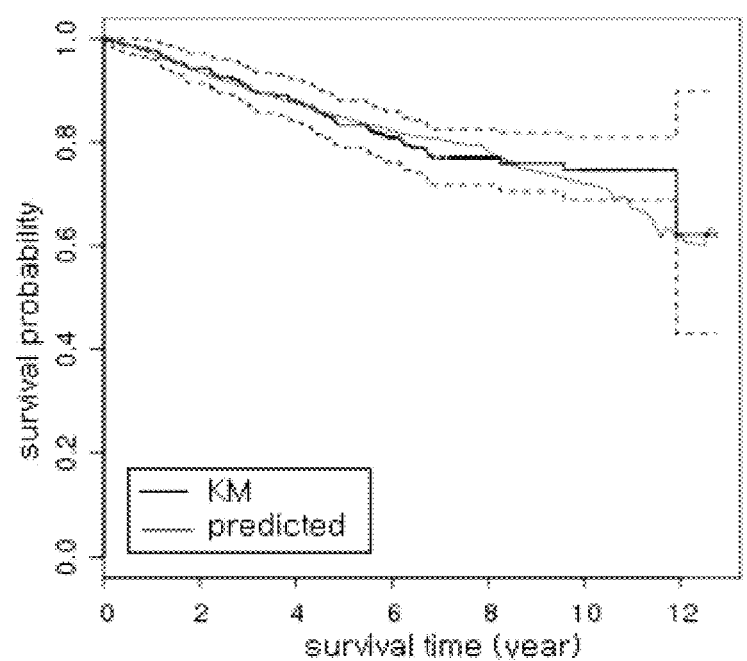
Figure 10C:
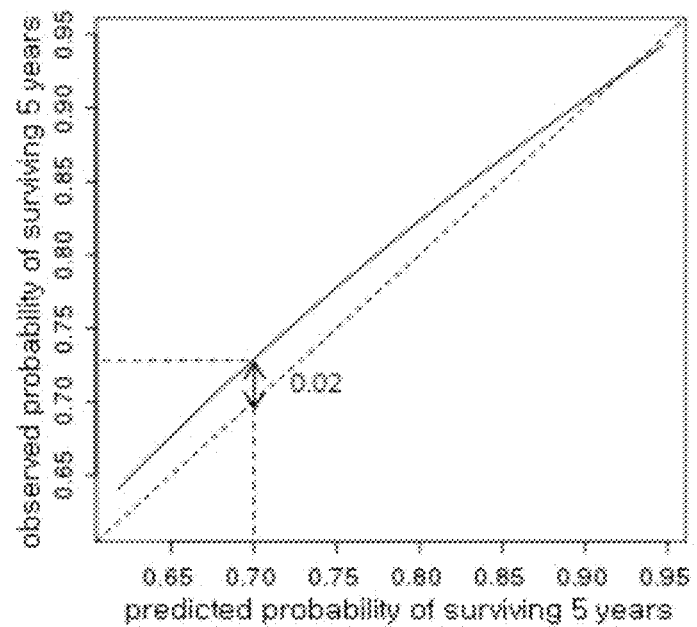
Figure 11A:
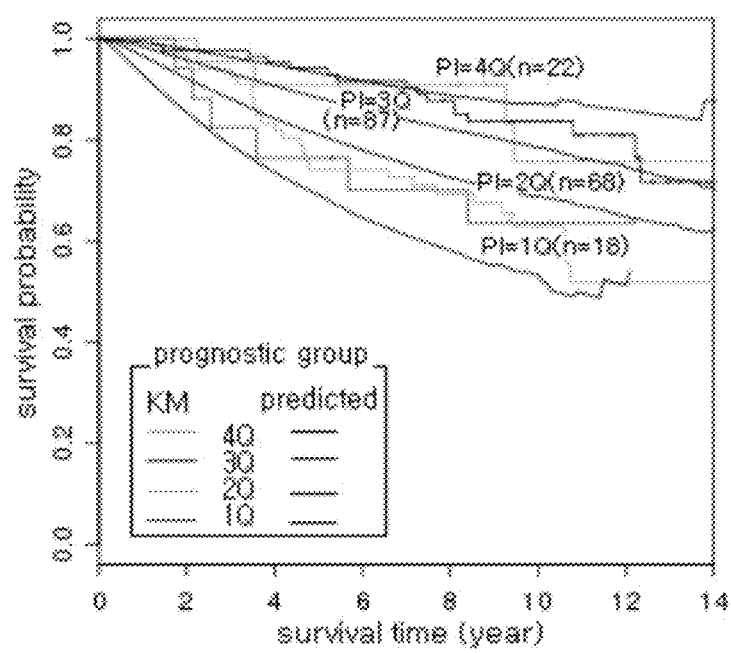
FIGS. 11a-11c represent verification results of the prognostic model in the validation set 2 and it is same verification method as the discovery set.
Figure 11B:
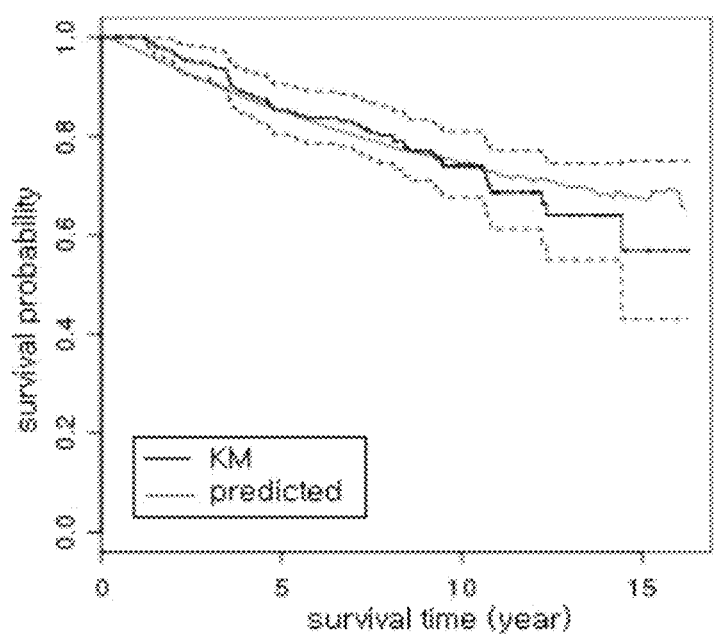
Figure 11C:
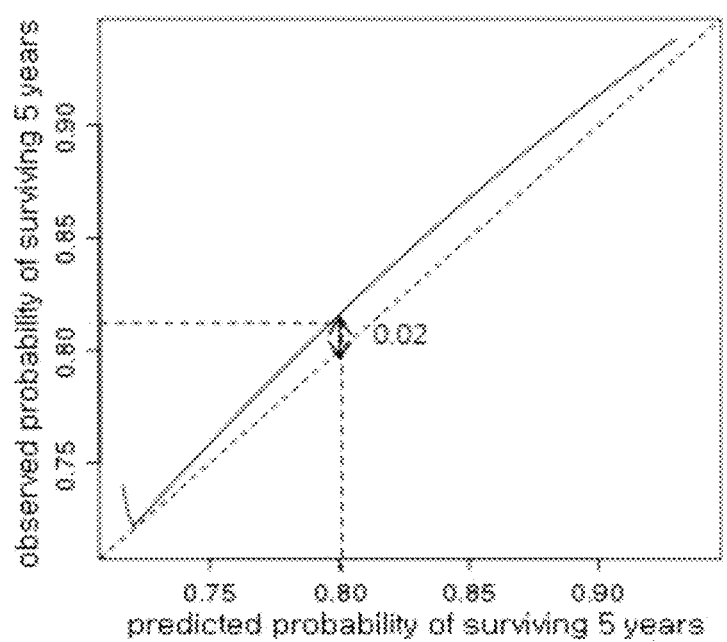
Figure 12:
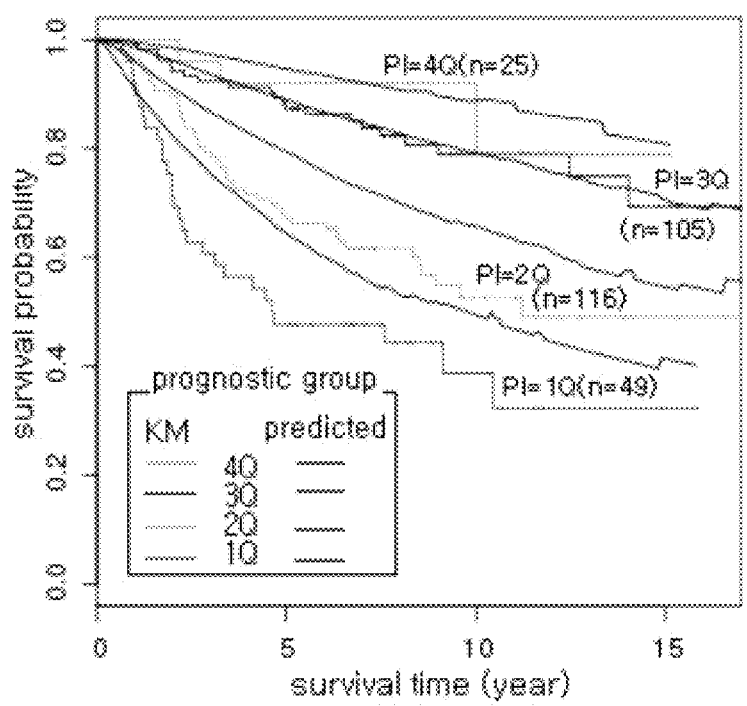
FIG. 12 represents verification results of the prognostic model in the validation set 3 and it is same verification method as the discovery set.

About 62% of ER− tumors were highly proliferating tumors (p3), while only 18% of ER+ tumors were highly proliferating (p3) supporting that ER− tumors tend to be more aggressive than ER+ tumors. In the same sense, about 35% of ER+ tumors were slowly growing tumors, but there were only 9% in ER− tumors. Predominant immune response was another characteristic of ER− tumors. About 38% of ER− tumors showed high activity of immune response (i3), while only 21% of ER+ tumors showed highly active immune response (i3) supporting the inhibition of ER on immune response (FIG. 2). Generally, high activity of proliferation accompanied increased activity of immune response in both ER statuses, but ER− tumors showed much more active immune response against fast proliferation.

Beside, a good correlation between histologic grade and proliferation was observed from the concentration of high grade (G3) along highly proliferating cases (p3) in both ER statuses. Deleterious effect of active proliferation on clinical prognosis was also observed in both ER statues from the high concentration of poor prognosis (development of distant-meta within 5 years) along highly proliferating cases (p3).

Overall, both of proliferation and immune response in ER− breast cancer were very active as compared to ER+ breast cancer, and it was supposed that ER expression levels influences in mechanisms of the generation and the development of breast cancer.

Development of a Prognostic Model with the p-Genes and i-Genes

Using the expression levels of the p-genes and i-genes, we developed a prognostic model for early breast cancer patients using the accelerated failure time (AFT) models. To reduce the number of candidate models, we roughly checked the distribution of hazard and the linearity of the selected variables. We fitted the hazard calculated from the life-table of the discovery data set to various distributions.

Since the hazard function obtained by the life table shows a form of unimodal, it was predicted that the Weibull, loglogistic and lognormal distributions would appropriate. Covariates included in the prognostic model are the p.mean and i.mean. p.mean is the average of the p-genes, and i.mean is the average of the i-genes.

As a result of applying the Weibull, loglogistic and lognormal distributions to three models, the lognormal distribution showed the best fit. Using AIC (Akaike's information criterion), the final model (3) was selected.

$$\log(T) = -0.689 \times p.mean + 0.274 \times i.mean + 3.219$$

According to the model, the p.mean showed a predominantly negative correlation (−0.689, p value=$2.47 \times e^{-17}$) with survival time (T) indicating that high activity of proliferation was corresponding to short survival time. In contrast to the p.mean, the i.mean showed positive correlation (0.274, p value=$3.69 \times e^{-11}$) with survival time (T) indicating that high activity of proliferation was corresponding to long survival time. Therefore, it could be understood that immune response act as the defense mechanism by immune response against high proliferation activity, whereas the proliferation play a pivotal role in breast cancer prognosis, and its high activity shows bad prognosis.

Verification of a Prognostic Model

The present inventors assessed the performance of the prognostic model in two ways, its 'calibration' and 'discrimination' aspects, using the expression profile to 1,072 of the early stage breast cancer patients in discovery dataset. 'Calibration' is the degree of correspondence between the estimated probability produced by the model and the actual observed probability. The actual observed probability refers to the corresponding Kaplan-Meier survival estimate. 'Discrimination' is the ability of the model to correctly separate the subjects into different groups. Verifications for calibration and determination to discovery dataset and three independent validation datasets were carried out.

4 prognostic groups were classified by dividing prognostic index (PI) into 4 areas to the discovery dataset developing prognostic model. 4 prognostic groups classified by prognostic index were compared using the KM graph as the observed survival probability. As a result, it could be determined that 4 prognostic groups were very well classified, and the predicted survival probability for each prognostic group corresponded well with the observed survival probability for each prognostic group.

KM survival probability and the survival probability predicted by the prognostic model were compared using graph. For each patient in the data set, the model was used to predict survival probabilities for all time points up to the date of the occurrence of distant-meta. The predicted survival probabilities were averaged over all cases in the sub set at each time point (from 0 to 25 by 0.1) to give a survival curve representative of the sub group. Using this method allows comparison of observed and predicted survival in groups of patients. The predicted survival probability was slightly higher than survival probability by KM, but they were similar overall. Together comparison of survival probability for the overall survival time, the survival probability for 5-year was also compared. The 5-year survival probability predicted by the model was similar to the actual observed 5-year survival probability. Particularly, the higher the predicted survival probability, it was showed the greater agreement with the observed survival probability.

Three independent validation datasets was subject to more objective verification for the prognostic model.

The first validation dataset is a pooled data set combined with two independent datasets generated with Affymetrix® U133A platform. The second validation dataset was the dataset generated by Affymetric® U133A platform, in which all patients were ER+ patients taking tamoxifen for five years. The third validation dataset was generated by Agilent Hu25K platform to use for developing and validating 70 prognostic genes (commercialized as MammaPrint®). The validation datasets 1 and 2 were generated with same platform, Affymetrix® U133A. The expression levels for the validation datasets 1, 2 and the discovery dataset were standardized. The validation datasets 1 and 2 assessed in terms of calibration and discrimination aspects. The validation datasets 3 assessed in terms of discrimination aspect, since it has a problem in the expression level of standardization.

In the validation dataset 1, 4 prognostic groups were clearly classified, and the predicted survival probability for each prognostic group corresponded well with the observed survival probability for each prognostic group. The predicted survival probability to overall time showed a good agreement with the observed KM graph, and the predicted survival probability at 5 years was higher than the observed survival probability by about 2%.

In the validation dataset 2, 4 prognostic groups were not clearly classified. However, overall, it was showed that the higher the predicted survival probability, the higher the observed survival probability. The predicted survival probability to overall time showed a good agreement with the observed KM graph, and the predicted survival probability at 5 years was higher than the observed survival probability by about 2%.

Having described a preferred embodiment of the present invention, it is to be understood that variants and modifications thereof falling within the spirit of the invention may become apparent to those skilled in this art, and the scope of this invention is to be determined by appended claims and their equivalents.

REFERENCES

1. Chang, H. Y., et al., Gene expression signature of fibroblast serum response predicts human cancer progression: similarities between tumors and wounds. PLoS Biol 2(2): p. E7 (2004).
2. van de Vijver, M. J., et al., A gene-expression signature as a predictor of survival in breast cancer. N Engl J Med 347(25):1999-2009 (2002).
3. van 't Veer, L. J., et al., Gene expression profiling predicts clinical prognosis of breast cancer. Nature 415(6871): 530-536 (2002).
4. Wang, Y., et al., Gene-expression profiles to predict distant metastasis of lymph-node-negative primary breast cancer. Lancet 365(9460): 671-679 (2005).
5. Buyse, M., et al., Validation and clinical utility of a 70-gene prognostic signature for women with node-negative breast cancer. J Natl Cancer Inst, 98(17):1183-92 (2006).
6. Paik, S., Development and clinical utility of a 21-gene recurrence score prognostic assay in patients with early breast cancer treated with tamoxifen. Oncologist 12(6): 631-635 (2007).
7. Paik, S., et al., A multigene assay to predict recurrence of tamoxifen-treated, node-negative breast cancer. N Engl J Med 351(27):2817-2826 (2004).
8. Sotiriou, C., et al., Gene expression profiling in breast cancer: understanding the molecular basis of histologic grade to improve prognosis. J Natl Cancer Inst 98(4):262-72 (2006)
9. Pawitan, Y., et al., Gene expression profiling spares early breast cancer patients from adjuvant therapy: derived and validated in two population-based cohorts. Breast Cancer Res 7(6):R953-964 (2005).
10. Miller, L. D., et al., An expression signature for p53 status in human breast cancer predicts mutation status, transcriptional effects, and patient survival. Proc Natl Acad Sci USA, 102(38):13550-13555 (2005).
11. Bild, A. H., et al., Oncogenic pathway signatures in human cancers as a guide to targeted therapies. Nature 439(7074):353-357 (2006).
12. Teschendorff, A. E., et al., A consensus prognostic gene expression classifier for ER positive breast cancer. Genome Biol 7(10):R101 (2006).
13. Desmedt, C., et al., Strong time dependence of the 76-gene prognostic signature for node-negative breast cancer patients in the TRANSBIG multicenter independent validation series. Clin Cancer Res 13(11): 3207-3214 (2007).
14. Kim, S. Y., Effects of sample size on robustness and prediction accuracy of a prognostic gene signature. BMC Bioinformatics 10:147 (2009).
15. Hummel, M., et al., Association between a prognostic gene signature and functional gene sets. Bioinform Biol Insights 2:329-341 (2008).
16. Pfeffer, U., et al., Prediction of breast cancer metastasis by genomic profiling: where do we stand? Clin Exp Metastasis 26(6): 547-558 (2009).
17. Ein-Dor, L., O. Zuk, and E. Domany, Thousands of samples are needed to generate a robust gene list for predicting prognosis in cancer. Proc Natl Acad Sci USA, 103(15):5923-5928 (2006).
18. van Vliet, M. H., et al., Pooling breast cancer datasets has a synergetic effect on classification performance and improves signature stability. BMC Genomics, 9:375 (2008).
19. Yasrebi, H., et al., Can survival prediction be improved by merging gene expression data sets? PLoS One 4(10): e7431 (2009).
20. Fan, C., et al., Concordance among gene-expression-based predictors for breast cancer. N Engl J Med 355(6): 560-569 (2006).
21. Reyal, F., et al., A comprehensive analysis of prognostic signatures reveals the high predictive capacity of the proliferation, immune response and RNA splicing modules in breast cancer. Breast Cancer Res 10(6):R93 (2008).
22. Yu, J. X., et al., Pathway analysis of gene signatures predicting metastasis of node-negative primary breast cancer. BMC Cancer 7:182 (2007).
23. Kim, S. Y. and Y. S. Kim, A gene sets approach for identifying prognostic gene signatures for prognosis prediction. BMC Genomics 9:177 (2008).
24. Thomassen, M., Q. Tan, and T. A. Kruse, Gene expression meta-analysis identifies metastatic pathways and transcription factors in breast cancer. BMC Cancer 8:394 (2008).
25. Schmidt, M., et al., The humoral immune system has a key prognostic impact in node-negative breast cancer. Cancer Res 68(13):5405-13 (2008).
26. Schmidt, M., et al., Coordinates in the universe of node-negative breast cancer revisited. Cancer Res 69(7): 2695-2698 (2009).
27. Calabro, A., et al., Effects of infiltrating lymphocytes and estrogen receptor on gene expression and prognosis in breast cancer. Breast Cancer Res Treat 116(1):69-77 (2009).
28. Finak, G., et al., Stromal gene expression predicts clinical prognosis in breast cancer. Nat Med 14(5):518-27 (2008).
29. Ma, X. J., et al., Gene expression profiling of the tumor microenvironment during breast cancer progression. Breast Cancer Res 11(1):R7 (2009).
30. Rutqvist, L. E., A. Wallgren, and B. Nilsson, Is breast cancer a curable disease? A study of 14,731 women with breast cancer from the Cancer Registry of Norway. Cancer 53(8):1793-1800 (1984).
31. Mould, R. F. and J. W. Boag, A test of several parametic statistical models for estimating success rate in the treatment of carcinoma cervix uteri. Br J Cancer 32(5):529-550 (1975).
32. Loi, S., et al., Predicting prognosis using molecular profiling in estrogen receptor-positive breast cancer treated with tamoxifen. BMC Genomics, 9:239 (2008).
33. Zhang, Y., et al., The 76-gene signature defines high-risk patients that benefit from adjuvant tamoxifen therapy. Breast Cancer Res Treat 116(2):303-309 (2009).
34. Dai, M., et al., Evolving gene/transcript definitions significantly alter the interpretation of Gene Chip data. Nucleic Acids Res 33(20):e175 (2005).
35. Tusher, V. G., R. Tibshirani, and G. Chu, Significance analysis of microarrays applied to the ionizing radiation response. Proc Natl Acad Sci USA, 98(9):5116-21 (2001).

The invention claimed is:

1. A method of treating a breast cancer in a breast cancer patient, comprising:
   collecting a breast cancer tissue sample from the breast cancer patient;
   isolating RNA from the breast cancer tissue sample;
   making cDNA with primers which specifically amplify a target sequence of SEQ ID NO: 7, complementary to the RNA from the breast cancer tissue sample;
   amplifying the cDNA with the primers;
   measuring an expression level of the target nucleotide sequence;
   comparing the measured expression level of the target nucleotide sequence to an expression level of said target nucleotide sequence in a reference breast tumor sample;
   diagnosing the breast cancer patient with an increased likelihood of metastasis of breast cancer, when the measured expression level of the target sequence is decreased in the breast cancer tissue sample as compared to the reference breast tumor sample; and
   treating the diagnosed breast cancer patient with at least one of chemotherapy and surgery.

2. The method according to claim 1, wherein the method further comprises:
   measuring the expression level of estrogen receptor (ER) of the breast cancer patient;
   comparing the measured expression level of ER of the breast cancer patient to a reference expression level of ER; and
   diagnosing the breast cancer patient with an increased likelihood of metastasis of breast cancer when the measured expression level of ER of the breast cancer patient is decreased compared to the reference expression level.

3. The method according to claim 1, wherein the method further comprises:
   making cDNA with primers which specifically amplify at least one target sequence selected from SEQ ID NO: 1, 2, 3, 4, 5, 6, 8 and 9, complementary to the RNA from the breast cancer tissue sample;
   amplifying the cDNA with the primers;
   measuring an expression level of the at least one target nucleotide sequence;
   comparing the measured expression level of the at least one target nucleotide sequence to an expression level of said at least one target nucleotide sequence in a reference breast tumor sample; and
   diagnosing the breast cancer patient with an increased likelihood of metastasis of breast cancer (i) when the measured expression of at least one target nucleotide sequence selected from the group consisting of SEQ ID NOS: 1, 2, 3 and 4 is increased in the breast cancer tissue sample as compared to the reference breast tumor sample, and/or (ii) when the measured expression level of the at least one target nucleotide sequence selected from the group consisting of SEQ ID NOS: 5, 6, 8 and 9 is decreased in the breast cancer tissue sample as compared to the reference breast tumor sample.

* * * * *